(12) United States Patent
Harris et al.

(10) Patent No.: US 11,399,834 B2
(45) Date of Patent: Aug. 2, 2022

(54) TISSUE APPOSITION CLIP APPLICATION METHODS

(71) Applicant: Ethicon Endo-Surgery, Inc., Cincinnati, OH (US)

(72) Inventors: Jason L. Harris, Lebanon, OH (US); James T. Spivey, Whitehouse Station, NJ (US)

(73) Assignee: Cilag GmbH International, Zug (CH)

( * ) Notice: Subject to any disclaimer, the term of this patent is extended or adjusted under 35 U.S.C. 154(b) by 533 days.

(21) Appl. No.: 16/166,833

(22) Filed: Oct. 22, 2018

(65) Prior Publication Data
US 2019/0053805 A1  Feb. 21, 2019

Related U.S. Application Data

(60) Continuation of application No. 14/515,023, filed on Oct. 15, 2014, now Pat. No. 10,105,141, which is a
(Continued)

(51) Int. Cl.
*A61B 17/10* (2006.01)
*A61B 17/08* (2006.01)
(Continued)

(52) U.S. Cl.
CPC ............ *A61B 17/10* (2013.01); *A61B 17/083* (2013.01); *A61B 17/105* (2013.01); *A61B 17/29* (2013.01); *A61B 2017/00818* (2013.01)

(58) Field of Classification Search
CPC . A61B 17/064; A61B 17/068; A61B 17/0682; A61B 17/072; A61B 17/07207;
(Continued)

(56) References Cited

U.S. PATENT DOCUMENTS

| 112,794 A | 3/1871 | Felton |
| 645,576 A | 3/1900 | Tesla |

(Continued)

FOREIGN PATENT DOCUMENTS

| AU | 666310 B2 | 2/1996 |
| DE | 19713797 A1 | 10/1997 |

(Continued)

OTHER PUBLICATIONS

Ethicon, Inc., "Wound Closure Manual: Chapters (The Surgical Needle)," 15 pages, (1994).
(Continued)

*Primary Examiner* — Dianne Dornbusch

(57) ABSTRACT

Surgical methods for closing a gastrotomy. The surgical method for closing an opening in an organ wall comprises positioning a distal end portion of a steerable overtube adjacent a portion of the organ wall through which the opening extends. The surgical method further comprises inserting a flexible clip magazine into the steerable overtube. The surgical method comprises grasping tissue through which the opening extends and drawing a portion of the grasped tissue into a clamping position between upper and lower clip arms of a distal-most tissue apposition clip supported within a distal end of the clip magazine. The surgical method further comprises advancing the distal-most tissue apposition clip onto the portion of grasped tissue.

12 Claims, 13 Drawing Sheets

Related U.S. Application Data division of application No. 12/172,766, filed on Jul. 14, 2008, now Pat. No. 8,888,792.

(51) Int. Cl.
  *A61B 17/29* (2006.01)
  *A61B 17/00* (2006.01)

(58) Field of Classification Search
  CPC ............ A61B 17/12222; A61B 17/128; A61B 17/1285; A61B 17/122; A61B 17/1227; A61B 17/10; A61B 17/083; A61B 17/105; A61B 17/29; A61B 2017/0053; A61B 2017/0487; A61B 2017/0488; A61B 2017/0688; A61B 2017/072; A61B 2017/07271; A61B 2017/00818
  See application file for complete search history.

(56) References Cited

U.S. PATENT DOCUMENTS

| | | |
|---|---|---|
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,330,147 A | 2/1920 | Stitzer |
| 1,330,205 A | 2/1920 | McKeehan |
| 1,335,331 A | 3/1920 | Gunderson |
| 1,440,116 A | 12/1922 | Telfer |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould |
| 1,892,018 A | 12/1932 | Stanton |
| 1,916,722 A | 7/1933 | Ende |
| 2,028,635 A | 1/1936 | Wappler |
| 2,031,682 A | 2/1936 | Wappler |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,303,961 A | 12/1942 | Sprague |
| 2,330,120 A | 9/1943 | Hagelstein |
| 2,388,137 A | 10/1945 | Graumlich |
| 2,409,379 A | 10/1946 | Mosaly |
| 2,451,077 A | 10/1948 | Emsig |
| 2,493,108 A | 1/1950 | Casey |
| 2,504,152 A | 4/1950 | Riker |
| 2,514,698 A | 7/1950 | Herrero |
| 2,514,951 A | 7/1950 | Herndon |
| 2,644,210 A | 7/1953 | McNamee |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,110,956 A | 11/1963 | Fischer, Jr. |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,543,760 A | 12/1970 | Bolduc |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,854,743 A | 12/1974 | Hansen |
| 3,929,123 A | 12/1975 | Jamshidi |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,043,342 A | 8/1977 | Morrison, Jr. |
| 4,071,028 A | 1/1978 | Perkins |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Oglu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,394,791 A | 7/1983 | Groth |
| 4,396,021 A | 8/1983 | Baumgartner |
| 4,396,139 A | 8/1983 | Hall et al. |
| 4,406,656 A | 9/1983 | Hattier et al. |
| 4,452,246 A | 6/1984 | Bader et al. |
| 4,461,281 A | 7/1984 | Carson |
| 4,491,132 A | 1/1985 | Aikins |
| 4,491,135 A | 1/1985 | Klein |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,239 A | 12/1987 | Sorochenko et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A * | 12/1988 | Tucker ................. A61B 17/083 227/120 |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |

(56) References Cited

U.S. PATENT DOCUMENTS

| | | |
|---|---|---|
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Slice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,015,249 A | 5/1991 | Nakao et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,049,153 A | 9/1991 | Nakao et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,099,827 A | 3/1992 | Melzer et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,156,151 A | 10/1992 | Imran |
| 5,156,609 A | 10/1992 | Nakao et al. |
| 5,174,300 A | 12/1992 | Bales et al. |
| 5,176,126 A | 1/1993 | Chikama |
| 5,180,373 A | 1/1993 | Green et al. |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,961 A | 6/1993 | Nakao et al. |
| 5,222,965 A | 6/1993 | Haughton |
| 5,224,946 A | 7/1993 | Hayhurst et al. |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,254,130 A | 10/1993 | Poncet et al. |
| 5,256,149 A | 10/1993 | Banik et al. |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,308,327 A | 5/1994 | Heaven et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Rath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A | 8/1994 | Durgin, Jr. et al. |
| 5,339,805 A | 8/1994 | Parker |
| 5,341,815 A | 8/1994 | Cotone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,368,606 A | 11/1994 | Marlow et al. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,378,234 A | 1/1995 | Hammerslag et al. |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,367 A | 3/1995 | Wilk |
| 5,395,381 A | 3/1995 | Green et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,326 A | 4/1995 | Harrison et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |

(56) References Cited

U.S. PATENT DOCUMENTS

| | | |
|---|---|---|
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schulken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,524,633 A | 6/1996 | Heaven et al. |
| 5,527,321 A | 6/1996 | Hinchliffe |
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,205 A | 10/1996 | Hart et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,611,803 A | 3/1997 | Heaven et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkier et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,665,096 A | 9/1997 | Yoon |
| 5,665,100 A | 9/1997 | Yoon |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,688,269 A | 11/1997 | Newton et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |

(56) References Cited

U.S. PATENT DOCUMENTS

| | | |
|---|---|---|
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,748 A | 7/1998 | Palmer et al. |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Muller et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,108 A | 10/1998 | Poncet |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |
| 5,843,097 A | 12/1998 | Mayenberger et al. |
| 5,843,121 A | 12/1998 | Yoon |
| 5,843,156 A | 12/1998 | Slepian et al. |
| 5,846,238 A | 12/1998 | Jackson et al. |
| 5,848,986 A | 12/1998 | Lundquist et al. |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,885,280 A | 3/1999 | Nettekoven et al. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,919,207 A | 7/1999 | Taheri |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,938,668 A | 8/1999 | Scirica et al. |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,933 A | 11/1999 | Yoon |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,090 A | 5/2000 | Yoon |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |

(56) References Cited

U.S. PATENT DOCUMENTS

| | | |
|---|---|---|
| 6,074,408 A | 6/2000 | Freeman |
| 6,086,530 A | 7/2000 | Mack |
| 6,086,600 A | 7/2000 | Kortenbach |
| 6,090,105 A | 7/2000 | Zepeda et al. |
| 6,090,107 A | 7/2000 | Borgmeier et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,701 A | 9/2000 | Nezhat |
| 6,123,718 A | 9/2000 | Tu et al. |
| 6,131,790 A | 10/2000 | Piraka |
| 6,139,555 A | 10/2000 | Hart et al. |
| 6,139,562 A | 10/2000 | Mauze et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A | 11/2000 | Foley et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,167,297 A | 12/2000 | Benaron |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,183,469 B1 | 2/2001 | Thapliyal et al. |
| 6,187,026 B1 | 2/2001 | Devlin et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,248,124 B1 | 6/2001 | Pedros et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,280,379 B1 | 8/2001 | Resnick |
| 6,283,963 B1 | 9/2001 | Regula |
| 6,287,304 B1 | 9/2001 | Eggers et al. |
| 6,293,909 B1 | 9/2001 | Chu et al. |
| 6,293,952 B1 | 9/2001 | Brosens et al. |
| 6,296,630 B1 | 10/2001 | Altman et al. |
| 6,306,131 B1 | 10/2001 | Hareyama et al. |
| 6,306,159 B1 | 10/2001 | Schwartz et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,346,092 B1 | 2/2002 | Leschinsky |
| 6,350,267 B1 | 2/2002 | Stefanchik |
| 6,350,269 B1 | 2/2002 | Shipp et al. |
| 6,350,278 B1 | 2/2002 | Lenker et al. |
| 6,352,503 B1 | 3/2002 | Matsui et al. |
| 6,352,541 B1 | 3/2002 | Kienzle et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,444 B1 | 9/2002 | Avni et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,074 B1 | 10/2002 | Matsui et al. |
| 6,458,076 B1 | 10/2002 | Pruitt |
| 6,464,697 B1 | 10/2002 | Edwards et al. |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,516,500 B2 | 2/2003 | Ogino et al. |
| 6,517,534 B1 | 2/2003 | McGovern et al. |
| 6,520,954 B2 | 2/2003 | Ouchi |
| 6,526,320 B2 | 2/2003 | Mitchell |
| 6,527,753 B2 | 3/2003 | Sekine et al. |
| 6,527,782 B2 | 3/2003 | Hogg et al. |
| 6,530,880 B2 | 3/2003 | Pagliuca |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |

(56) References Cited

U.S. PATENT DOCUMENTS

| | | |
|---|---|---|
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,085 B2 | 5/2003 | Kortenbach et al. |
| 6,569,091 B2 | 5/2003 | Diokno et al. |
| 6,569,120 B1 | 5/2003 | Green et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,594,971 B1 | 7/2003 | Addy et al. |
| 6,602,262 B2 | 8/2003 | Griego et al. |
| 6,605,105 B1 | 8/2003 | Cuschieri et al. |
| 6,607,529 B1 | 8/2003 | Jones et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,171 B2 | 10/2003 | Iddan et al. |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |
| 6,662,035 B2 | 12/2003 | Sochor |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,070 B2 | 1/2004 | Edwards et al. |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,684,938 B2 | 2/2004 | Tsujita et al. |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,695,867 B2 | 2/2004 | Ginn et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,352 B2 | 7/2004 | Field et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chomenky et al. |
| 6,800,056 B2 | 10/2004 | Tartaglia et al. |
| 6,808,491 B2 | 10/2004 | Kortenbach et al. |
| 6,814,697 B2 | 11/2004 | Ouchi |
| 6,814,739 B2 | 11/2004 | Secrest et al. |
| 6,817,974 B2 | 11/2004 | Cooper et al. |
| 6,818,007 B1 | 11/2004 | Dampney et al. |
| 6,821,285 B2 | 11/2004 | Laufer et al. |
| 6,824,548 B2 | 11/2004 | Smith et al. |
| 6,830,545 B2 | 12/2004 | Bendall |
| 6,830,578 B2 | 12/2004 | O'Heeron et al. |
| 6,835,200 B2 | 12/2004 | Laufer et al. |
| 6,836,688 B2 | 12/2004 | Ingle et al. |
| 6,837,847 B2 | 1/2005 | Ewers et al. |
| 6,837,886 B2 | 1/2005 | Collins et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,852,078 B2 | 2/2005 | Ouchi |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,869,395 B2 | 3/2005 | Page et al. |
| 6,869,398 B2 | 3/2005 | Obenchain et al. |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,911,019 B2 | 6/2005 | Muller et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,921,408 B2 | 7/2005 | Sauer |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizard et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |

(56) References Cited

U.S. PATENT DOCUMENTS

| | | |
|---|---|---|
| 6,939,347 B2 | 9/2005 | Thompson |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,949,105 B2 | 9/2005 | Bryan et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,980,854 B2 | 12/2005 | Bernabei |
| 6,980,858 B2 | 12/2005 | Fuimaono et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,705 B2 | 2/2006 | Nobis et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,004,957 B1 | 2/2006 | Dampney et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,115,785 B2 | 10/2006 | Guggenheim et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,122,605 B2 | 10/2006 | Ohrbom et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,713 B2 | 12/2006 | Shener et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Muller et al. |
| 7,160,296 B2 | 1/2007 | Pearson et al. |
| 7,163,525 B2 | 1/2007 | Franer |
| 7,169,104 B2 | 1/2007 | Ueda et al. |
| 7,169,115 B2 | 1/2007 | Nobis et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,179,262 B2 | 2/2007 | Bryan et al. |
| 7,186,265 B2 | 3/2007 | Sharkawy et al. |
| 7,188,627 B2 | 3/2007 | Nelson et al. |
| 7,189,231 B2 | 3/2007 | Clague et al. |
| 7,195,612 B2 | 3/2007 | van Sloten et al. |
| 7,195,631 B2 | 3/2007 | Dumbauld |
| 7,204,804 B2 | 4/2007 | Zirps et al. |
| 7,204,820 B2 | 4/2007 | Akahoshi |
| 7,204,840 B2 | 4/2007 | Skakoon et al. |
| 7,207,997 B2 | 4/2007 | Shipp et al. |
| 7,208,005 B2 | 4/2007 | Frecker et al. |
| 7,211,089 B2 | 5/2007 | Kear et al. |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francese et al. |
| 7,226,458 B2 | 6/2007 | Kaplan et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,084 B2 | 6/2007 | Skakoon et al. |
| 7,235,089 B1 | 6/2007 | McGuckin, Jr. |
| 7,241,290 B2 | 7/2007 | Doyle et al. |
| 7,241,295 B2 | 7/2007 | Maguire |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,261,728 B2 | 8/2007 | Long et al. |
| 7,270,663 B2 | 9/2007 | Nakao |
| 7,278,179 B2 | 10/2007 | Schneider |
| 7,288,075 B2 | 10/2007 | Parihar et al. |

(56) References Cited

U.S. PATENT DOCUMENTS

| | | |
|---|---|---|
| 7,290,615 B2 | 11/2007 | Christanti et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,331,968 B2 | 2/2008 | Arp et al. |
| 7,335,220 B2 | 2/2008 | Khosravi et al. |
| 7,338,513 B2 | 3/2008 | Lee et al. |
| 7,341,554 B2 | 3/2008 | Sekine et al. |
| 7,344,536 B1 | 3/2008 | Lunsford et al. |
| 7,349,223 B2 | 3/2008 | Haemer et al. |
| 7,352,387 B2 | 4/2008 | Yamamoto |
| 7,357,802 B2 | 4/2008 | Palanker et al. |
| 7,357,806 B2 | 4/2008 | Rivera et al. |
| 7,364,582 B2 | 4/2008 | Lee |
| 7,367,939 B2 | 5/2008 | Smith et al. |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,431,694 B2 | 10/2008 | Stefanchik et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,514,568 B2 | 4/2009 | Freeman |
| 7,515,953 B2 | 4/2009 | Madar et al. |
| 7,520,876 B2 | 4/2009 | Ressemann et al. |
| 7,520,950 B2 | 4/2009 | Saadat et al. |
| 7,524,281 B2 | 4/2009 | Chu et al. |
| 7,524,302 B2 | 4/2009 | Tower |
| 7,534,228 B2 | 5/2009 | Williams |
| 7,535,570 B2 | 5/2009 | Muraishi |
| 7,536,217 B2 | 5/2009 | Minai et al. |
| 7,540,872 B2 | 6/2009 | Schechter et al. |
| 7,542,807 B2 | 6/2009 | Bertolero et al. |
| 7,544,195 B2 | 6/2009 | Lunsford et al. |
| 7,544,203 B2 | 6/2009 | Chin et al. |
| 7,547,310 B2 | 6/2009 | Whitfield |
| 7,548,040 B2 | 6/2009 | Lee et al. |
| 7,549,564 B2 | 6/2009 | Boudreaux |
| 7,549,990 B2 | 6/2009 | Canady |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,300 B2 | 7/2009 | Devierre et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,578,832 B2 | 8/2009 | Johnson et al. |
| 7,579,005 B2 | 8/2009 | Keeler et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,588,585 B2 | 9/2009 | Gold et al. |
| 7,591,781 B2 | 9/2009 | Hirata |
| 7,591,783 B2 | 9/2009 | Boulais et al. |
| 7,597,229 B2 | 10/2009 | Boudreaux et al. |
| 7,604,150 B2 | 10/2009 | Boudreaux |
| 7,604,633 B2 | 10/2009 | Truckai et al. |
| 7,608,083 B2 | 10/2009 | Lee et al. |
| 7,611,479 B2 | 11/2009 | Cragg et al. |
| 7,612,084 B2 | 11/2009 | James et al. |
| 7,615,002 B2 | 11/2009 | Rothweiler et al. |
| 7,615,003 B2 | 11/2009 | Stefanchik et al. |
| 7,615,005 B2 | 11/2009 | Stefanchik et al. |
| 7,615,058 B2 | 11/2009 | Sixto, Jr. et al. |
| 7,615,067 B2 | 11/2009 | Lee et al. |
| 7,618,398 B2 | 11/2009 | Holman et al. |
| 7,618,437 B2 | 11/2009 | Nakao |
| 7,621,910 B2 | 11/2009 | Sugi |
| 7,621,927 B2 | 11/2009 | Messerly et al. |
| 7,621,936 B2 | 11/2009 | Cragg et al. |
| 7,628,792 B2 | 12/2009 | Guerra |
| 7,628,797 B2 | 12/2009 | Tieu et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,637,905 B2 | 12/2009 | Saadat et al. |
| 7,645,288 B2 | 1/2010 | McKenna et al. |
| 7,648,457 B2 | 1/2010 | Stefanchik et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,658,738 B2 | 2/2010 | Nobis et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,670,346 B2 | 3/2010 | Whitfield |
| 7,674,259 B2 | 3/2010 | Shadduck |
| 7,674,275 B2 | 3/2010 | Martin et al. |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,691,103 B2 | 4/2010 | Fernandez et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,704,248 B2 | 4/2010 | DiCarlo |
| 7,708,756 B2 | 5/2010 | Nobis et al. |
| 7,710,563 B2 | 5/2010 | Betzig et al. |
| 7,713,189 B2 | 5/2010 | Hanke |
| 7,713,270 B2 | 5/2010 | Suzuki |
| 7,717,847 B2 | 5/2010 | Smith |
| 7,721,742 B2 | 5/2010 | Kalloo et al. |
| 7,722,631 B2 | 5/2010 | Mikkaichi et al. |
| 7,727,242 B2 | 6/2010 | Sepetka et al. |

(56) References Cited

U.S. PATENT DOCUMENTS

| | | |
|---|---|---|
| 7,727,246 B2 | 6/2010 | Sixto, Jr. et al. |
| 7,727,248 B2 | 6/2010 | Smith et al. |
| 7,727,249 B2 | 6/2010 | Rahmani |
| 7,731,697 B2 | 6/2010 | Porter et al. |
| 7,731,725 B2 | 6/2010 | Gadberry et al. |
| 7,736,191 B1 | 6/2010 | Sochor |
| 7,736,360 B2 | 6/2010 | Mody et al. |
| 7,736,374 B2 | 6/2010 | Vaughan et al. |
| 7,744,591 B2 | 6/2010 | Rioux et al. |
| 7,744,613 B2 | 6/2010 | Ewers et al. |
| 7,744,615 B2 | 6/2010 | Couture |
| 7,749,161 B2 | 7/2010 | Beckman et al. |
| 7,749,163 B2 | 7/2010 | Mulac et al. |
| 7,751,866 B2 | 7/2010 | Aoki et al. |
| 7,751,869 B2 | 7/2010 | Rioux et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,758,598 B2 | 7/2010 | Conlon et al. |
| 7,762,949 B2 | 7/2010 | Nakao |
| 7,762,959 B2 | 7/2010 | Bilsbury |
| 7,762,960 B2 | 7/2010 | Timberlake et al. |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,819 B2 | 8/2010 | Matsumoto |
| 7,766,896 B2 | 8/2010 | Kornkven Volk et al. |
| 7,770,584 B2 | 8/2010 | Danek et al. |
| 7,771,396 B2 | 8/2010 | Stefanchik et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,639 B2 | 8/2010 | Van Lue |
| 7,780,683 B2 | 8/2010 | Roue et al. |
| 7,780,691 B2 | 8/2010 | Stefanchik |
| 7,784,663 B2 | 8/2010 | Shelton, IV |
| 7,785,348 B2 | 8/2010 | Kuhns et al. |
| 7,789,825 B2 | 9/2010 | Nobis et al. |
| 7,789,827 B2 | 9/2010 | Landry |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,798,750 B2 | 9/2010 | Clark |
| 7,798,960 B2 | 9/2010 | Jaeger |
| 7,803,163 B2 | 9/2010 | Skakoon |
| 7,803,195 B2 | 9/2010 | Levy et al. |
| 7,813,590 B2 | 10/2010 | Horn et al. |
| 7,813,789 B2 | 10/2010 | Glukhovsky |
| 7,815,565 B2 | 10/2010 | Stefanchik et al. |
| 7,815,566 B2 | 10/2010 | Stefanchik et al. |
| 7,815,651 B2 | 10/2010 | Skakoon et al. |
| 7,815,652 B2 | 10/2010 | Messerly et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,819,872 B2 | 10/2010 | Johnson et al. |
| 7,828,186 B2 | 11/2010 | Wales |
| 7,828,793 B2 | 11/2010 | Thompson et al. |
| 7,828,808 B2 | 11/2010 | Hinman et al. |
| 7,828,809 B2 | 11/2010 | Skakoon et al. |
| 7,833,156 B2 | 11/2010 | Williams et al. |
| 7,833,231 B2 | 11/2010 | Skakoon et al. |
| 7,833,238 B2 | 11/2010 | Nakao |
| 7,837,615 B2 | 11/2010 | Le et al. |
| 7,842,028 B2 | 11/2010 | Lee |
| 7,842,050 B2 | 11/2010 | Diduch et al. |
| 7,842,068 B2 | 11/2010 | Ginn |
| 7,846,087 B2 | 12/2010 | Stefanchik et al. |
| 7,846,107 B2 | 12/2010 | Hoffman et al. |
| 7,846,171 B2 | 12/2010 | Kullas et al. |
| 7,850,660 B2 | 12/2010 | Uth et al. |
| 7,850,686 B2 | 12/2010 | Nobis et al. |
| 7,850,712 B2 | 12/2010 | Conlon et al. |
| 7,857,183 B2 | 12/2010 | Shelton, IV |
| 7,857,820 B2 | 12/2010 | Skakoon et al. |
| 7,862,546 B2 | 1/2011 | Conlon et al. |
| 7,862,553 B2 | 1/2011 | Ewaschuk |
| 7,862,572 B2 | 1/2011 | Meade et al. |
| 7,862,582 B2 | 1/2011 | Ortiz et al. |
| 7,867,216 B2 | 1/2011 | Wahr et al. |
| 7,871,371 B2 | 1/2011 | Komiya et al. |
| 7,875,042 B2 | 1/2011 | Martin et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,550 B2 | 2/2011 | Daglow et al. |
| 7,887,558 B2 | 2/2011 | Lin et al. |
| 7,892,200 B2 | 2/2011 | Birk et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,905,830 B2 | 3/2011 | Stefanchik et al. |
| 7,909,809 B2 | 3/2011 | Scopton et al. |
| 7,914,513 B2 | 3/2011 | Voorhees, Jr. |
| 7,916,809 B2 | 3/2011 | Tsushima |
| 7,918,783 B2 | 4/2011 | Maseda et al. |
| 7,918,785 B2 | 4/2011 | Okada et al. |
| 7,918,844 B2 | 4/2011 | Byrum et al. |
| 7,918,845 B2 | 4/2011 | Saadat et al. |
| 7,918,848 B2 | 4/2011 | Lau et al. |
| 7,918,869 B2 | 4/2011 | Saadat et al. |
| 7,922,650 B2 | 4/2011 | McWeeney et al. |
| 7,922,717 B2 | 4/2011 | Sugita |
| 7,922,739 B2 | 4/2011 | Downey |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,931,661 B2 | 4/2011 | Saadat et al. |
| 7,935,130 B2 | 5/2011 | Williams |
| 7,937,143 B2 | 5/2011 | Demarais et al. |
| 7,945,332 B2 | 5/2011 | Schechter |
| 7,947,000 B2 | 5/2011 | Vargas et al. |
| 7,951,073 B2 | 5/2011 | Freed |
| 7,953,326 B2 | 5/2011 | Farr et al. |
| 7,955,298 B2 | 6/2011 | Carroll et al. |
| 7,955,340 B2 | 6/2011 | Michlitsch et al. |
| 7,955,355 B2 | 6/2011 | Chin |
| 7,959,627 B2 | 6/2011 | Utley et al. |
| 7,959,629 B2 | 6/2011 | Young et al. |
| 7,959,642 B2 | 6/2011 | Nobis et al. |
| 7,963,192 B2 | 6/2011 | Mayenberger et al. |
| 7,963,912 B2 | 6/2011 | Zwolinski et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,967,842 B2 | 6/2011 | Bakos |
| 7,969,473 B2 | 6/2011 | Kotoda |
| 7,972,330 B2 | 7/2011 | Alejandro et al. |
| 7,972,333 B2 | 7/2011 | Nishimura |
| 7,976,458 B2 | 7/2011 | Stefanchik et al. |
| 7,976,552 B2 | 7/2011 | Suzuki |
| 7,985,239 B2 | 7/2011 | Suzuki |
| 7,985,830 B2 | 7/2011 | Mance et al. |
| 7,988,618 B2 | 8/2011 | Mikkaichi et al. |
| 7,988,685 B2 | 8/2011 | Ziaie et al. |
| 7,988,690 B2 | 8/2011 | Chanduszko et al. |
| 7,998,132 B2 | 8/2011 | Gregorich et al. |
| 8,007,474 B2 | 8/2011 | Uth et al. |
| 8,007,495 B2 | 8/2011 | McDaniel et al. |
| 8,021,340 B2 | 9/2011 | Porter et al. |
| 8,021,358 B2 | 9/2011 | Doyle et al. |
| 8,021,362 B2 | 9/2011 | Deem et al. |
| 8,021,378 B2 | 9/2011 | Sixto, Jr. et al. |
| 8,027,710 B1 | 9/2011 | Dannan |
| 8,029,504 B2 | 10/2011 | Long |
| 8,034,046 B2 | 10/2011 | Eidenschink |
| 8,037,591 B2 | 10/2011 | Spivey et al. |
| 8,038,596 B2 | 10/2011 | Miyake et al. |
| 8,038,612 B2 | 10/2011 | Paz |
| 8,043,289 B2 | 10/2011 | Behl et al. |
| 8,048,060 B2 | 11/2011 | Griffin et al. |

(56) References Cited

U.S. PATENT DOCUMENTS

| | | |
|---|---|---|
| 8,048,067 B2 | 11/2011 | Davalos et al. |
| 8,048,108 B2 | 11/2011 | Sibbitt, Jr. et al. |
| 8,052,597 B2 | 11/2011 | Boulais |
| 8,052,699 B1 | 11/2011 | Sherwinter |
| 8,057,462 B2 | 11/2011 | Weitzner et al. |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Rittman, III et al. |
| 8,070,743 B2 | 12/2011 | Kagan et al. |
| 8,070,759 B2 | 12/2011 | Stefanchik et al. |
| 8,070,804 B2 | 12/2011 | Hyde et al. |
| 8,075,478 B2 | 12/2011 | Campos |
| 8,075,567 B2 | 12/2011 | Taylor et al. |
| 8,075,572 B2 | 12/2011 | Stefanchik et al. |
| 8,075,573 B2 | 12/2011 | Gambale et al. |
| 8,075,587 B2 | 12/2011 | Ginn |
| 8,083,787 B2 | 12/2011 | Korb et al. |
| 8,088,062 B2 | 1/2012 | Zwolinski |
| 8,092,374 B2 | 1/2012 | Smith et al. |
| 8,092,549 B2 | 1/2012 | Hillis et al. |
| 8,096,459 B2 | 1/2012 | Ortiz et al. |
| 8,096,941 B2 | 1/2012 | Fowler et al. |
| 8,096,998 B2 | 1/2012 | Cresina |
| 8,097,001 B2 | 1/2012 | Nakao |
| 8,100,922 B2 | 1/2012 | Griffith |
| 8,105,342 B2 | 1/2012 | Onuki et al. |
| 8,109,872 B2 | 2/2012 | Kennedy, II et al. |
| 8,109,919 B2 | 2/2012 | Kraft et al. |
| 8,109,926 B2 | 2/2012 | Azure |
| 8,114,072 B2 | 2/2012 | Long et al. |
| 8,114,113 B2 | 2/2012 | Becker |
| 8,114,119 B2 | 2/2012 | Spivey et al. |
| 8,115,447 B2 | 2/2012 | Toya et al. |
| 8,118,738 B2 | 2/2012 | Larkin |
| 8,118,821 B2 | 2/2012 | Mouw |
| 8,118,834 B1 | 2/2012 | Goraltchouk et al. |
| 8,118,835 B2 | 2/2012 | Weisel et al. |
| 8,123,677 B2 | 2/2012 | Fujimori |
| 8,131,371 B2 | 3/2012 | Demarals et al. |
| 8,147,424 B2 | 4/2012 | Kassab et al. |
| 8,157,813 B2 | 4/2012 | Ko et al. |
| 8,157,817 B2 | 4/2012 | Bonadio et al. |
| 8,157,834 B2 | 4/2012 | Conlon |
| 8,159,549 B2 | 4/2012 | Glukhovsky et al. |
| 8,166,615 B2 | 5/2012 | Coldiron |
| 8,167,894 B2 | 5/2012 | Miles et al. |
| 8,172,772 B2 | 5/2012 | Zwolinski et al. |
| 8,172,839 B2 | 5/2012 | Kato |
| 8,182,414 B2 | 5/2012 | Handa et al. |
| 8,187,166 B2 | 5/2012 | Kuth et al. |
| 8,200,334 B1 | 6/2012 | Min et al. |
| 8,202,265 B2 | 6/2012 | Boulais |
| 8,202,295 B2 | 6/2012 | Kaplan |
| 8,206,295 B2 | 6/2012 | Kaul |
| 8,211,119 B2 | 7/2012 | Palmer et al. |
| 8,211,125 B2 | 7/2012 | Spivey |
| 8,212,861 B2 | 7/2012 | Takahashi et al. |
| 8,216,224 B2 | 7/2012 | Morris et al. |
| 8,216,252 B2 | 7/2012 | Vaughan et al. |
| 8,216,255 B2 | 7/2012 | Smith et al. |
| 8,221,310 B2 | 7/2012 | Saadat et al. |
| 8,221,411 B2 | 7/2012 | Francischelli et al. |
| 8,222,385 B2 | 7/2012 | Yoshizaki et al. |
| 8,241,204 B2 | 8/2012 | Spivey |
| 8,241,309 B2 | 8/2012 | Miles et al. |
| 8,246,633 B2 | 8/2012 | Omori |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,674 B2 | 9/2012 | Daglow et al. |
| 8,262,680 B2 | 9/2012 | Swain et al. |
| 8,267,854 B2 | 9/2012 | Asada et al. |
| 8,269,823 B2 | 9/2012 | Hirakawa et al. |
| 8,277,373 B2 | 10/2012 | Maahs et al. |
| 8,282,665 B2 | 10/2012 | Kieturakis et al. |
| 8,298,161 B2 | 10/2012 | Vargas |
| 8,303,485 B2 | 11/2012 | Segawa et al. |
| 8,303,581 B2 | 11/2012 | Arts et al. |
| 8,308,682 B2 | 11/2012 | Kramer et al. |
| 8,308,738 B2 | 11/2012 | Nobis et al. |
| 8,308,743 B2 | 11/2012 | Matsuno et al. |
| 8,313,496 B2 | 11/2012 | Sauer et al. |
| 8,315,714 B2 | 11/2012 | Daglow et al. |
| 8,317,806 B2 | 11/2012 | Coe et al. |
| 8,317,814 B2 | 11/2012 | Karasawa et al. |
| 8,328,836 B2 | 12/2012 | Conlon et al. |
| 8,333,691 B2 | 12/2012 | Schaaf |
| 8,333,777 B2 | 12/2012 | Schaller et al. |
| 8,337,394 B2 | 12/2012 | Vakharia |
| 8,337,492 B2 | 12/2012 | Kunis et al. |
| 8,337,510 B2 | 12/2012 | Rieber et al. |
| 8,343,041 B2 | 1/2013 | Byers et al. |
| 8,348,827 B2 | 1/2013 | Zwolinski |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,366,606 B2 | 2/2013 | Watanabe et al. |
| 8,366,733 B2 | 2/2013 | Gabel et al. |
| 8,377,044 B2 | 2/2013 | Coe et al. |
| 8,377,057 B2 | 2/2013 | Rick et al. |
| 8,382,790 B2 | 2/2013 | Uenohara et al. |
| 8,388,653 B2 | 3/2013 | Nobis et al. |
| 8,394,090 B2 | 3/2013 | Ootsubo |
| 8,397,335 B2 | 3/2013 | Gordin et al. |
| 8,403,926 B2 | 3/2013 | Nobis et al. |
| 8,409,076 B2 | 4/2013 | Pang et al. |
| 8,409,197 B2 | 4/2013 | Slater |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 | 6/2013 | Demarais et al. |
| 8,460,275 B2 | 6/2013 | Taylor et al. |
| 8,465,419 B2 | 6/2013 | Moriyama |
| 8,465,484 B2 | 6/2013 | Davalos et al. |
| 8,469,993 B2 | 6/2013 | Berg et al. |
| 8,475,359 B2 | 7/2013 | Asada et al. |
| 8,475,361 B2 | 7/2013 | Barlow et al. |
| 8,475,452 B2 | 7/2013 | Van Wyk et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,512,335 B2 | 8/2013 | Cheng et al. |
| 8,517,921 B2 | 8/2013 | Tremaglio et al. |
| 8,518,024 B2 | 8/2013 | Williams et al. |
| 8,518,052 B2 | 8/2013 | Burgermeister et al. |
| 8,518,062 B2 | 8/2013 | Cole et al. |
| 8,523,884 B2 | 9/2013 | Stam et al. |
| 8,523,939 B1 | 9/2013 | Hausen |
| 8,529,563 B2 | 9/2013 | Long et al. |
| 8,540,744 B2 | 9/2013 | Spivey et al. |
| 8,545,396 B2 | 10/2013 | Cover et al. |
| 8,545,450 B2 | 10/2013 | Voegele et al. |
| 8,551,058 B2 | 10/2013 | Measamer et al. |
| 8,562,513 B2 | 10/2013 | Yamatani |
| 8,562,602 B2 | 10/2013 | Azure |
| 8,568,410 B2 | 10/2013 | Vakharia et al. |
| 8,579,176 B2 | 11/2013 | Smith et al. |
| 8,579,897 B2 | 11/2013 | Vakharia et al. |
| 8,585,644 B2 | 11/2013 | Rodriguez Lelis et al. |
| 8,602,970 B2 | 12/2013 | Muyari et al. |
| 8,603,138 B2 | 12/2013 | Faller et al. |
| 8,608,652 B2 | 12/2013 | Voegele et al. |
| 8,617,156 B2 | 12/2013 | Werneth et al. |
| 8,623,011 B2 | 1/2014 | Spivey |

(56) References Cited

U.S. PATENT DOCUMENTS

| | | |
|---|---|---|
| 8,632,534 B2 | 1/2014 | Pearson et al. |
| 8,632,563 B2 | 1/2014 | Nagase et al. |
| 8,636,648 B2 | 1/2014 | Gazdzinski |
| 8,636,650 B2 | 1/2014 | Lee |
| 8,636,730 B2 | 1/2014 | Keppel |
| 8,640,940 B2 | 2/2014 | Ohdaira |
| 8,641,728 B2 | 2/2014 | Stokes et al. |
| 8,652,150 B2 | 2/2014 | Swain et al. |
| 8,657,174 B2 | 2/2014 | Yates et al. |
| 8,663,236 B2 | 3/2014 | Chen et al. |
| 8,663,263 B2 | 3/2014 | Smith |
| 8,668,686 B2 | 3/2014 | Govari et al. |
| 8,678,999 B2 | 3/2014 | Isaacson |
| 8,679,003 B2 | 3/2014 | Spivey |
| 8,679,096 B2 | 3/2014 | Farritor et al. |
| 8,684,967 B2 | 4/2014 | Engel et al. |
| 8,685,058 B2 | 4/2014 | Wilk |
| 8,702,753 B2 | 4/2014 | Mikkaichi et al. |
| 8,704,923 B2 | 4/2014 | Ogasawara et al. |
| 8,715,281 B2 | 5/2014 | Barlow et al. |
| 8,721,658 B2 | 5/2014 | Kahle et al. |
| 8,723,936 B2 | 5/2014 | Amling et al. |
| 8,727,967 B2 | 5/2014 | Weitzner |
| 8,738,141 B2 | 5/2014 | Smith et al. |
| 8,747,401 B2 | 6/2014 | Gonzalez et al. |
| 8,753,262 B2 | 6/2014 | Sugiyama et al. |
| 8,753,335 B2 | 6/2014 | Moshe et al. |
| 8,764,735 B2 | 7/2014 | Coe et al. |
| 8,771,173 B2 | 7/2014 | Fonger et al. |
| 8,771,260 B2 | 7/2014 | Conlon et al. |
| 8,774,913 B2 | 7/2014 | Demarais et al. |
| 8,784,403 B2 | 7/2014 | Cefai et al. |
| 8,784,436 B2 | 7/2014 | Ho et al. |
| 8,795,161 B2 | 8/2014 | Carter |
| 8,821,520 B2 | 9/2014 | Schwemberger et al. |
| 8,821,532 B2 | 9/2014 | Schaeffer |
| 8,828,031 B2 | 9/2014 | Fox et al. |
| 8,834,461 B2 | 9/2014 | Werneth et al. |
| 8,845,656 B2 | 9/2014 | Skakoon et al. |
| 8,858,590 B2 | 10/2014 | Shelton, IV et al. |
| 8,876,701 B2 | 11/2014 | Surti et al. |
| 8,876,772 B2 | 11/2014 | Weber et al. |
| 8,880,185 B2 | 11/2014 | Hastings et al. |
| 8,882,786 B2 | 11/2014 | Bearinger et al. |
| 8,888,792 B2 | 11/2014 | Harris et al. |
| 8,894,633 B2 | 11/2014 | Farritor et al. |
| 8,906,035 B2 | 12/2014 | Zwolinski et al. |
| 8,911,452 B2 | 12/2014 | Skakoon et al. |
| 8,920,442 B2 | 12/2014 | Sibbitt, Jr. et al. |
| 8,926,606 B2 | 1/2015 | Davalos et al. |
| 8,932,208 B2 | 1/2015 | Kendale et al. |
| 8,939,897 B2 | 1/2015 | Nobis |
| 8,939,969 B2 | 1/2015 | Temelli et al. |
| 8,956,352 B2 | 2/2015 | Mauch et al. |
| 8,974,374 B2 | 3/2015 | Schostek et al. |
| 8,979,751 B2 | 3/2015 | George |
| 8,986,199 B2 | 3/2015 | Weisenburgh, II et al. |
| 8,986,343 B2 | 3/2015 | Bourque et al. |
| 8,992,517 B2 | 3/2015 | Davalos et al. |
| 9,005,198 B2 | 4/2015 | Long et al. |
| 9,011,431 B2 | 4/2015 | Long et al. |
| 9,028,483 B2 | 5/2015 | Long et al. |
| 9,036,015 B2 | 5/2015 | Verburgh et al. |
| 9,044,247 B2 | 6/2015 | Kato |
| 9,049,987 B2 | 6/2015 | Conlon et al. |
| 9,060,782 B2 | 6/2015 | Daniel et al. |
| 9,066,655 B2 | 6/2015 | Stefanchik et al. |
| 9,078,662 B2 | 7/2015 | Bakos et al. |
| 9,084,621 B2 | 7/2015 | Weitzner et al. |
| 9,089,323 B2 | 7/2015 | Bonutti et al. |
| 9,125,557 B2 | 9/2015 | Lien et al. |
| 9,125,631 B2 | 9/2015 | Smith et al. |
| 9,125,639 B2 | 9/2015 | Mathis et al. |
| 9,138,586 B2 | 9/2015 | Eiger |
| 9,149,172 B2 | 10/2015 | Iddan et al. |
| 9,155,587 B2 | 10/2015 | Willis et al. |
| 9,162,050 B2 | 10/2015 | Boling |
| 9,186,203 B2 | 11/2015 | Spivey et al. |
| 9,198,733 B2 | 12/2015 | Neal, II et al. |
| 9,220,526 B2 | 12/2015 | Conlon |
| 9,226,772 B2 | 1/2016 | Fox |
| 9,233,241 B2 | 1/2016 | Long |
| 9,248,278 B2 | 2/2016 | Crosby et al. |
| 9,254,169 B2 | 2/2016 | Long et al. |
| 9,265,407 B2 | 2/2016 | Goldfarb et al. |
| 9,271,796 B2 | 3/2016 | Buysse et al. |
| 9,277,957 B2 | 3/2016 | Long et al. |
| 9,295,485 B2 | 3/2016 | Conlon et al. |
| 9,308,049 B2 | 4/2016 | Dejima |
| 9,314,620 B2 | 4/2016 | Long et al. |
| 9,339,264 B2 | 5/2016 | Piech et al. |
| 9,339,328 B2 | 5/2016 | Ortiz et al. |
| 9,345,462 B2 | 5/2016 | Weitzner et al. |
| 9,352,152 B2 | 5/2016 | Lindenthaler et al. |
| 9,364,278 B2 | 6/2016 | DeCarlo et al. |
| 9,370,341 B2 | 6/2016 | Ceniccola et al. |
| 9,375,268 B2 | 6/2016 | Long |
| 9,427,255 B2 | 8/2016 | Griffith et al. |
| 9,486,241 B2 | 11/2016 | Zeiner et al. |
| 9,492,148 B2 | 11/2016 | Ginn et al. |
| 9,545,290 B2 | 1/2017 | Tellio et al. |
| 9,549,719 B2 | 1/2017 | Shohat et al. |
| 9,566,126 B2 | 2/2017 | Weitzner et al. |
| 9,572,623 B2 | 2/2017 | Long |
| 9,596,980 B2 | 3/2017 | Marescaux et al. |
| 9,596,994 B2 | 3/2017 | Futrell et al. |
| 9,598,691 B2 | 3/2017 | Davalos |
| 9,627,120 B2 | 4/2017 | Scott et al. |
| 9,636,251 B2 | 5/2017 | Swann |
| 9,668,725 B2 | 6/2017 | Beaven |
| 9,694,175 B2 | 7/2017 | Tyson, Jr. |
| 9,700,334 B2 | 7/2017 | Hinman et al. |
| 9,788,885 B2 | 10/2017 | Long et al. |
| 9,788,888 B2 | 10/2017 | Bakos et al. |
| 9,788,890 B2 | 10/2017 | Toth et al. |
| 9,808,597 B2 | 11/2017 | Vargas et al. |
| 9,833,282 B2 | 12/2017 | Jun |
| 9,833,595 B2 | 12/2017 | Gonzalez |
| 9,861,272 B2 | 1/2018 | Pell et al. |
| 9,861,350 B2 | 1/2018 | Serina et al. |
| 9,867,652 B2 | 1/2018 | Sano et al. |
| 9,877,781 B2 | 1/2018 | Grasse et al. |
| 9,883,910 B2 | 2/2018 | Conlon et al. |
| 9,974,944 B2 | 5/2018 | Sudam et al. |
| 10,004,558 B2 | 6/2018 | Long et al. |
| 10,010,666 B2 | 7/2018 | Rubinsky et al. |
| 10,071,012 B2 | 9/2018 | Larson et al. |
| 10,092,291 B2 | 10/2018 | Voegele et al. |
| 10,098,527 B2 | 10/2018 | Weisenburgh, II et al. |
| 10,098,691 B2 | 10/2018 | Long et al. |
| 10,105,141 B2 | 10/2018 | Harris et al. |
| 10,206,709 B2 | 2/2019 | Griffith et al. |
| 10,208,158 B2 | 2/2019 | Banister et al. |
| 10,258,406 B2 | 4/2019 | Long |
| 10,278,761 B2 | 5/2019 | Long et al. |
| 10,300,268 B2 | 5/2019 | Skakoon et al. |
| 10,314,603 B2 | 6/2019 | Conlon |
| 10,314,649 B2 | 6/2019 | Bakos et al. |
| 10,321,927 B2 | 6/2019 | Hinman |
| 10,342,598 B2 | 7/2019 | Long et al. |
| 10,376,314 B2 | 8/2019 | van der Weide et al. |
| 10,390,715 B2 | 8/2019 | Rich et al. |
| 10,448,989 B2 | 10/2019 | Arena et al. |
| 10,478,248 B2 | 11/2019 | Long |
| 10,492,880 B2 | 12/2019 | Tellio et al. |
| 10,660,632 B2 | 5/2020 | Torrie et al. |
| 2001/0023333 A1 | 9/2001 | Wise et al. |
| 2002/0019641 A1 | 2/2002 | Truwit |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0068945 A1 | 6/2002 | Sixto et al. |
| 2002/0082551 A1 | 6/2002 | Yachia et al. |

(56) References Cited

U.S. PATENT DOCUMENTS

| | | |
|---|---|---|
| 2002/0095164 A1 | 7/2002 | Andreas et al. |
| 2002/0133115 A1 | 9/2002 | Gordon et al. |
| 2002/0133178 A1* | 9/2002 | Muramatsu ........ A61B 17/1227 606/142 |
| 2002/0138086 A1 | 9/2002 | Sixto et al. |
| 2002/0165592 A1 | 11/2002 | Glukhovsky et al. |
| 2002/0173786 A1* | 11/2002 | Kortenbach ....... A61B 17/1227 606/45 |
| 2002/0198541 A1 | 12/2002 | Smith et al. |
| 2003/0014090 A1 | 1/2003 | Abrahamson |
| 2003/0018373 A1 | 1/2003 | Eckhardt et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0093104 A1 | 5/2003 | Bonner et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0170898 A1 | 9/2003 | Gundersen et al. |
| 2003/0181900 A1 | 9/2003 | Long |
| 2003/0187351 A1 | 10/2003 | Franck et al. |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2004/0002683 A1 | 1/2004 | Nicholson et al. |
| 2004/0024414 A1 | 2/2004 | Downing |
| 2004/0045133 A1 | 3/2004 | Buettell |
| 2004/0054377 A1 | 3/2004 | Foster et al. |
| 2004/0092970 A1 | 5/2004 | Xavier |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0133089 A1 | 7/2004 | Kilcoyne et al. |
| 2004/0136779 A1 | 7/2004 | Bhaskar |
| 2004/0138529 A1 | 7/2004 | Wiltshire et al. |
| 2004/0138587 A1 | 7/2004 | Lyons |
| 2004/0138747 A1 | 7/2004 | Kaladelfos |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0225186 A1 | 11/2004 | Horne et al. |
| 2004/0243108 A1 | 12/2004 | Suzuki |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260315 A1 | 12/2004 | Dell et al. |
| 2004/0260337 A1 | 12/2004 | Freed |
| 2005/0000553 A1 | 1/2005 | Noguchi et al. |
| 2005/0004515 A1 | 1/2005 | Hart et al. |
| 2005/0010211 A1 | 1/2005 | Suzuki |
| 2005/0015103 A1 | 1/2005 | Popov |
| 2005/0043690 A1 | 2/2005 | Todd |
| 2005/0059963 A1 | 3/2005 | Phan et al. |
| 2005/0059964 A1 | 3/2005 | Fitz |
| 2005/0065509 A1 | 3/2005 | Coldwell et al. |
| 2005/0070947 A1 | 3/2005 | Franer et al. |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131457 A1 | 6/2005 | Douglas et al. |
| 2005/0137454 A1 | 6/2005 | Saadat et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0165272 A1 | 7/2005 | Okada et al. |
| 2005/0165378 A1 | 7/2005 | Heinrich et al. |
| 2005/0165411 A1 | 7/2005 | Orban |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192602 A1 | 9/2005 | Manzo |
| 2005/0209624 A1 | 9/2005 | Vijay |
| 2005/0215858 A1 | 9/2005 | Vail |
| 2005/0216036 A1 | 9/2005 | Nakao |
| 2005/0222495 A1 | 10/2005 | Okada et al. |
| 2005/0228224 A1 | 10/2005 | Okada et al. |
| 2005/0228406 A1 | 10/2005 | Bose |
| 2005/0240249 A1 | 10/2005 | Tu et al. |
| 2005/0250987 A1 | 11/2005 | Ewers et al. |
| 2005/0251176 A1 | 11/2005 | Swanstrom et al. |
| 2005/0256524 A1 | 11/2005 | Long et al. |
| 2005/0261711 A1* | 11/2005 | Okada ................ A61B 17/0401 606/153 |
| 2005/0267492 A1 | 12/2005 | Poncet et al. |
| 2005/0272977 A1 | 12/2005 | Saadat et al. |
| 2005/0274935 A1 | 12/2005 | Nelson |
| 2005/0277956 A1 | 12/2005 | Francese et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0025654 A1 | 2/2006 | Suzuki et al. |
| 2006/0025781 A1 | 2/2006 | Young et al. |
| 2006/0025812 A1 | 2/2006 | Shelton |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0064083 A1 | 3/2006 | Khalaj et al. |
| 2006/0069424 A1 | 3/2006 | Acosta et al. |
| 2006/0069429 A1 | 3/2006 | Spence et al. |
| 2006/0074413 A1 | 4/2006 | Behzadian |
| 2006/0089528 A1 | 4/2006 | Tartaglia et al. |
| 2006/0095031 A1 | 5/2006 | Ormsby |
| 2006/0100687 A1 | 5/2006 | Fahey et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0161190 A1 | 7/2006 | Gadberry et al. |
| 2006/0167482 A1 | 7/2006 | Swain et al. |
| 2006/0173452 A1 | 8/2006 | Buysse et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0200005 A1 | 9/2006 | Bjork et al. |

(56) References Cited

U.S. PATENT DOCUMENTS

| | | |
|---|---|---|
| 2006/0200121 A1 | 9/2006 | Mowery |
| 2006/0200169 A1 | 9/2006 | Sniffin |
| 2006/0200170 A1 | 9/2006 | Aranyi |
| 2006/0217665 A1 | 9/2006 | Prosek |
| 2006/0217742 A1 | 9/2006 | Messerly et al. |
| 2006/0237023 A1 | 10/2006 | Cox et al. |
| 2006/0241570 A1 | 10/2006 | Wilk |
| 2006/0241691 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0253004 A1 | 11/2006 | Frisch et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0287644 A1 | 12/2006 | Inganas et al. |
| 2006/0287666 A1 | 12/2006 | Saadat et al. |
| 2007/0000550 A1 | 1/2007 | Osinski |
| 2007/0005019 A1 | 1/2007 | Okishige |
| 2007/0015965 A1 | 1/2007 | Cox et al. |
| 2007/0032701 A1 | 2/2007 | Fowler et al. |
| 2007/0051375 A1 | 3/2007 | Milliman |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0078439 A1 | 4/2007 | Grandt et al. |
| 2007/0083192 A1 | 4/2007 | Welch |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106317 A1 | 5/2007 | Shelton et al. |
| 2007/0112251 A1 | 5/2007 | Nakhuda |
| 2007/0112342 A1 | 5/2007 | Pearson et al. |
| 2007/0112385 A1 | 5/2007 | Conlon |
| 2007/0112417 A1 | 5/2007 | Shanley et al. |
| 2007/0118115 A1 | 5/2007 | Artale et al. |
| 2007/0123840 A1 | 5/2007 | Cox |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0156028 A1 | 7/2007 | Van Lue et al. |
| 2007/0161855 A1 | 7/2007 | Mikkaichi et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0191904 A1 | 8/2007 | Libbus et al. |
| 2007/0198057 A1 | 8/2007 | Gelbart et al. |
| 2007/0203398 A1 | 8/2007 | Bonadio et al. |
| 2007/0208336 A1 | 9/2007 | Kim et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0233040 A1 | 10/2007 | Macnamara et al. |
| 2007/0244356 A1 | 10/2007 | Carrillo et al. |
| 2007/0244358 A1 | 10/2007 | Lee |
| 2007/0255303 A1 | 11/2007 | Bakos et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270907 A1 | 11/2007 | Stokes et al. |
| 2007/0282165 A1 | 12/2007 | Hopkins et al. |
| 2008/0004650 A1 | 1/2008 | George |
| 2008/0004656 A1 | 1/2008 | Livneh |
| 2008/0015413 A1 | 1/2008 | Barlow et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0058586 A1 | 3/2008 | Karpiel |
| 2008/0065169 A1 | 3/2008 | Colliou et al. |
| 2008/0082108 A1 | 4/2008 | Skakoon et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0103527 A1 | 5/2008 | Martin et al. |
| 2008/0114384 A1 | 5/2008 | Chang et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0140069 A1 | 6/2008 | Filloux et al. |
| 2008/0140071 A1 | 6/2008 | Vegesna |
| 2008/0150754 A1 | 6/2008 | Quendt |
| 2008/0171907 A1 | 7/2008 | Long et al. |
| 2008/0177141 A1 | 7/2008 | Wu et al. |
| 2008/0188710 A1 | 8/2008 | Segawa et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0214890 A1 | 9/2008 | Motai et al. |
| 2008/0215070 A1 | 9/2008 | Gildenberg |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0243148 A1 | 10/2008 | Mikkaichi et al. |
| 2008/0255647 A1 | 10/2008 | Jensen et al. |
| 2008/0262513 A1 | 10/2008 | Stabler et al. |
| 2008/0262524 A1 | 10/2008 | Bangera et al. |
| 2008/0262540 A1 | 10/2008 | Bangera et al. |
| 2008/0287801 A1 | 11/2008 | Magnin et al. |
| 2008/0294159 A1 | 11/2008 | Akahoshi et al. |
| 2008/0300458 A1 | 12/2008 | Kim et al. |
| 2008/0300461 A1 | 12/2008 | Shaw et al. |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2008/0312502 A1 | 12/2008 | Swain et al. |
| 2009/0018396 A1 | 1/2009 | Takizawa et al. |
| 2009/0030278 A1 | 1/2009 | Minakuchi |
| 2009/0048486 A1 | 2/2009 | Surti |
| 2009/0054728 A1 | 2/2009 | Rusty |
| 2009/0062788 A1 | 3/2009 | Long et al. |
| 2009/0062795 A1 | 3/2009 | Vakharia et al. |
| 2009/0069786 A1 | 3/2009 | Vesely et al. |
| 2009/0076536 A1 | 3/2009 | Rentschler et al. |
| 2009/0078736 A1 | 3/2009 | Van Lue |
| 2009/0082627 A1 | 3/2009 | Karasawa et al. |
| 2009/0093690 A1 | 4/2009 | Yoshizawa |
| 2009/0099414 A1 | 4/2009 | Goto et al. |
| 2009/0112059 A1 | 4/2009 | Nobis |
| 2009/0112063 A1 | 4/2009 | Bakos et al. |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0198251 A1 | 8/2009 | Ransbury et al. |
| 2009/0209804 A1 | 8/2009 | Seiler et al. |
| 2009/0210000 A1 | 8/2009 | Sullivan et al. |
| 2009/0221873 A1 | 9/2009 | McGrath |
| 2009/0228001 A1 | 9/2009 | Pacey |
| 2009/0234278 A1 | 9/2009 | Eck |
| 2009/0254019 A1 | 10/2009 | Gehl et al. |
| 2009/0259105 A1 | 10/2009 | Miyano et al. |

(56) References Cited

U.S. PATENT DOCUMENTS

| | | |
|---|---|---|
| 2009/0281559 A1 | 11/2009 | Swain et al. |
| 2009/0287045 A1 | 11/2009 | Mitelberg et al. |
| 2009/0287236 A1 | 11/2009 | Bakos et al. |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0016878 A1 | 1/2010 | Smith |
| 2010/0023032 A1 | 1/2010 | Granja Filho |
| 2010/0036198 A1 | 2/2010 | Tacchino et al. |
| 2010/0048990 A1 | 2/2010 | Bakos |
| 2010/0049223 A1 | 2/2010 | Granja Filho |
| 2010/0056862 A1 | 3/2010 | Bakos |
| 2010/0076451 A1 | 3/2010 | Zwolinski et al. |
| 2010/0081875 A1 | 4/2010 | Fowler et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0160906 A1 | 6/2010 | Jarrard |
| 2010/0191050 A1 | 7/2010 | Zwolinski |
| 2010/0191267 A1 | 7/2010 | Fox |
| 2010/0198248 A1 | 8/2010 | Vakharia |
| 2010/0210906 A1 | 8/2010 | Wendlandt |
| 2010/0217367 A1 | 8/2010 | Belson |
| 2010/0229610 A1 | 9/2010 | Garrigan et al. |
| 2010/0249700 A1 | 9/2010 | Spivey |
| 2010/0268025 A1 | 10/2010 | Belson |
| 2010/0280368 A1 | 11/2010 | Can et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2011/0077476 A1 | 3/2011 | Rofougaran et al. |
| 2011/0087224 A1 | 4/2011 | Cadeddu et al. |
| 2011/0087265 A1 | 4/2011 | Nobis et al. |
| 2011/0093009 A1 | 4/2011 | Fox |
| 2011/0098694 A1 | 4/2011 | Long |
| 2011/0098704 A1 | 4/2011 | Long et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Rusty |
| 2011/0152610 A1 | 6/2011 | Trusty et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0224663 A1 | 9/2011 | Heim et al. |
| 2011/0245619 A1 | 10/2011 | Holcomb |
| 2011/0284014 A1 | 11/2011 | Cadeddu et al. |
| 2011/0288547 A1 | 11/2011 | Morgan et al. |
| 2011/0306840 A1 | 12/2011 | Allen et al. |
| 2011/0313415 A1 | 12/2011 | Fernandez et al. |
| 2012/0005939 A1 | 1/2012 | Vandewalle |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0116155 A1 | 5/2012 | Trusty |
| 2012/0116266 A1 | 5/2012 | Houser et al. |
| 2012/0149981 A1 | 6/2012 | Khait et al. |
| 2012/0191075 A1 | 7/2012 | Trusty |
| 2012/0197246 A1 | 8/2012 | Mauch |
| 2013/0030430 A1 | 1/2013 | Stewart et al. |
| 2013/0030462 A1 | 1/2013 | Keating et al. |
| 2013/0090666 A1 | 4/2013 | Hess et al. |
| 2013/0158348 A1 | 6/2013 | Nobis et al. |
| 2013/0245356 A1 | 9/2013 | Fernandez et al. |
| 2013/0267834 A1 | 10/2013 | McGee |
| 2013/0331649 A1 | 12/2013 | Khait et al. |
| 2014/0014024 A1 | 1/2014 | Schroeder |
| 2014/0052216 A1 | 2/2014 | Long et al. |
| 2014/0121678 A1 | 5/2014 | Trusty et al. |
| 2015/0157293 A1 | 6/2015 | Shibamoto et al. |
| 2017/0049508 A1 | 2/2017 | Long et al. |
| 2017/0119465 A1 | 5/2017 | Long et al. |
| 2018/0303541 A1 | 10/2018 | Long et al. |
| 2018/0360535 A1 | 12/2018 | Long et al. |
| 2019/0117054 A1 | 4/2019 | Weisenburgh, II et al. |
| 2019/0321073 A1 | 10/2019 | Griffith et al. |

FOREIGN PATENT DOCUMENTS

| | | |
|---|---|---|
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 1281356 A2 | 2/2003 |
| EP | 0941128 B1 | 10/2004 |
| EP | 0848598 B1 | 2/2005 |
| EP | 1281360 B1 | 3/2005 |
| EP | 1153578 B1 | 3/2007 |
| EP | 1493397 B1 | 9/2011 |
| FR | 2731610 A1 | 9/1996 |
| GB | 330629 A | 6/1930 |
| JP | S63309252 A | 12/1988 |
| JP | H0438960 A | 2/1992 |
| JP | H0829699 A | 2/1996 |
| JP | H0975365 A | 3/1997 |
| JP | H1024049 A | 1/1998 |
| JP | 3007713 B2 | 2/2000 |
| JP | 2000245683 A | 9/2000 |
| JP | 2001526072 A | 12/2001 |
| JP | 2002369791 A | 12/2002 |
| JP | 2003088494 A | 3/2003 |
| JP | 2003235852 A | 8/2003 |
| JP | 2004033525 A | 2/2004 |
| JP | 2004065745 A | 3/2004 |
| JP | 2005121947 A | 5/2005 |
| JP | 2005261514 A | 9/2005 |
| JP | 2005296063 A | 10/2005 |
| JP | 2006297005 A | 11/2006 |
| JP | 2006343510 A | 12/2006 |
| JP | 2007125264 A | 5/2007 |
| JP | 5646674 B2 | 12/2014 |
| NL | 1021295 C2 | 2/2004 |
| SU | 194230 | 5/1967 |
| SU | 980703 A1 | 12/1982 |
| WO | WO-8607543 A1 | 12/1986 |
| WO | WO-9320765 A1 | 10/1993 |
| WO | WO-9712557 A1 | 4/1997 |
| WO | WO-9900060 A1 | 1/1999 |
| WO | WO-9917661 A1 | 4/1999 |
| WO | WO-9930622 A2 | 6/1999 |
| WO | WO-0126708 A1 | 4/2001 |
| WO | WO-0158360 A2 | 8/2001 |
| WO | WO-03081761 A2 | 10/2003 |
| WO | WO-2005018467 A2 | 3/2005 |
| WO | WO-2007013059 A2 | 2/2007 |
| WO | WO-2008102154 A2 | 8/2008 |
| WO | WO-2008151237 A1 | 12/2008 |
| WO | WO-2009029065 A1 | 3/2009 |
| WO | WO-2009032623 A2 | 3/2009 |

OTHER PUBLICATIONS

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).

(56) References Cited

OTHER PUBLICATIONS

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duetto Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
P. O'Neill, M.D. et al., "Nonsuture Intestinal Anastamosis," Am J. Surg, (1962), vol. 104, pp. 761-767.
C.P. Swain, M.D et al., "Anastomosis at Flexible Endoscopy: An Experimental Study of Compression Button Gastrojejunostomy," Gastrointest Endosc, (1991), vol. 37, pp. 628-632.
USGI® EndoSurgical Operating System - g-Prox® Tissue Grasper/Approximation Device; [online] URL: http://www.usgimedical.com/eos/components-gprox.htm - accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, August (2007), pp. 255-259.
D.B. Nelson, MD et al., "Endoscopic Hemostatic Devices," Gastrointestinal Endoscopy, vol. 54, No. 6, 2001, pp. 833-840.
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Evans, "Ablative and cathether-delivered therapies for colorectal liver metastases (Crlm)," Ejso, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Link et al., "Regional Chemotherapy of Nonresectable Colorectal Liver Metastases with Mitoxanthrone, 5-Fluorouracil, FolinicAcid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1 .htm; accessed online Nov. 1, 2011 (3 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Bewlay et al., "Spinning" in ASM Handbook, vol. 14B, Metalworking: Sheet Forming (2006).
Davalos, et al., "Tissue Ablation with Irreversible Electroporation," Annals of Biomedical Engineering, 33.2 (2005): 223-231.
Maxim Integrated Application Note 3977: Class D Amplifiers: Fundamentals of Operation and Recent Developments, Jan. 31, 2007.
Michael S. Kavic, M.D., "Natural Orifice Translumenal Endoscopic Surgery: "Notes"", Jsls, vol. 10, pp. 133-134 (2006).
Miklavcic et al., "A validated model of in vivo electric field distribution in tissues for electrochemotherapy and for DNA electrotransfer for gene therapy," Biochimica et Biophysica Acta, 1523, pp. 73-83 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time fora Randomized Trial?" Annals of Surgical Oncology, 15(1), pp. 144-157 (2008).
"Ethicon Endo-Surgery Studies Presented At DDW Demonstrate Potential Of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using A Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using A Magnetically Anchored Camera and Novel Instrumentation," Poster submitted along with Abstract at SAGES Annual Meeting in Phoenix, AZ, Apr. 22, 2009 (1 page).
Hakko Retractors, obtained Aug. 25, 2009 (5 pages).
Edd, et al., "In Vivo Results of a New Focal Tissue Ablation Technique: Irreversible Electroporation," IEEE Trans Biomed Eng, vol. 53, pp. 1409-1415, 2006.
Ogando, "Prototype Tools That Go With The Flow," Design News, 2 pages, Jul. 17, 2006.
CRET Pulmonary Balloon Dilator; [online] URL: http://www.bostonscientific.com/Device.bsci?page=HCP_Overview&navRel ld=1000.1003&metho d=D..., accessed Jul. 18, 2008 (4 pages).
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

(56) References Cited

OTHER PUBLICATIONS

Rutala et al. "Guideline for Disinfection and Sterilization in Healthcare Facilities, 2008" (available at http://www.cdc.gov/hicpac/Disinfection_Sterilization/13_11sterilizingPractices.html).

Z-Offset Technique Used in the Introduction of Trocar During Laparoscopic Surgery, M.S. Hershey NOTES Presentation to Ees Notes Development Team, Sep. 27, 2007.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

J.B. Murphy, M.D., "Cholecysto-lntestinal, Gastro-Intestinal, Entero-lntestinal Anastomosis, and Approximation Without Sutures (original research)," Med Rec, (Dec. 10, 1892), vol. 42(24), pp. 665-676.

Widera et al., "Increased DNA Vaccine Delivery and Immunogenicity by Electroporation In Vivo," The Journal of Immunology, 164, pp. 4635-4640 (2000).

Schoenbach et al. "Bacterial Decontamination of Liquids with Pulsed Electric Fields" IEEE Transactions on Dielectrics and Electrical Insulation. Vol. 7 No. 5. Oct. 2000, pp. 637-645.

Instant Armor: Science Videos—Science News—ScienCentral; http://www.sciencentral.com/articles./view.php3?article_id=218392121; accessed online Nov. 1, 2011 (2 pages).

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

Jolly et al., Properties and Applications of Commercial Magneto rheological Fluids. SPIE 5th Annual Int. Symposium on Smart Structures and Materials, 1998 (18 pages).

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

K.E. Mönkemüller, M.D., et al., "Transmural Drainage of Pancreatic Fluid Collections Without Electrocautery Using the Seidinger Technique," Gastrointestinal Endoscopy, vol. 48, No. 2, 1998, pp. 195-200, (Accepted Mar. 31, 1998).

\* cited by examiner

TISSUE APPOSITION CLIP APPLICATION METHODS

CROSS REFERENCE TO RELATED APPLICATIONS

This application is a continuation application claiming priority under 35 U.S.C. § 120 to U.S. patent application Ser. No. 14/515,023, entitled TISSUE APPOSITION CLIP APPLICATION METHODS, filed on Oct. 15, 2014, which issued on Oct. 23, 2018 as U.S. Pat. No. 10,105,141, which is a divisional application claiming priority under 35 U.S.C. § 121 to U.S. patent application Ser. No. 12/172,766, entitled TISSUE APPOSITION CLIP APPLICATION DEVICES AND METHODS, filed on Jul. 14, 2008, which issued on Nov. 18, 2014 as U.S. Pat. No. 8,888,792, the entire disclosures of which are hereby incorporated by reference herein.

FIELD OF THE INVENTION

The present invention relates, in general, to surgical devices and methods of use and, more particularly, to devices and methods for closing a hole or defect in a wall of tissue such as the wall of an organ.

BACKGROUND OF THE INVENTION

Access to the abdominal cavity may, from time to time, be required for diagnostic and therapeutic endeavors for a variety of medical and surgical diseases. Historically, abdominal access has required a formal laparotomy to provide adequate exposure. Such "open" procedures which require incisions to be made in the abdomen are not particularly well-suited for patients that may have extensive abdominal scarring from previous procedures, those persons who are morbidly obese, those individuals with abdominal wall infection, and those patients with diminished abdominal wall integrity, such as patients with burns and skin grafting. Other patients simply do not want to have a scar if it can be avoided.

Minimally invasive procedures are desirable because such procedures can reduce pain and provide relatively quick recovery times as compared with conventional open medical procedures. Many minimally invasive procedures are performed with a flexible or rigid endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. The trocar must pass through several layers of overlapping tissue/muscle before reaching the abdominal or peritoneal cavity. One of the most significant problems associated with such surgical procedures is the need to provide a secure closure of the peritoneal access site that is required for endoscope passage and, for example, specimen removal. Prior methods required the surgeon to close each of the muscle layers after the procedure is completed.

Still less invasive treatments include those that are performed through insertion of an endoscope through a natural body orifice to a treatment region such as, but not limited to within the peritoneal cavity. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as Natural Orifice Translumenal Endoscopic Surgery (NOTES)™. Examples of this approach include, but are not limited to, cystoscopy, hysteroscopy, esophagogastroduodenoscopy, and colonoscopy. However, those procedures that involve forming a hole or passage through tissue such as, but not limited to, the stomach, the colon, the vaginal wall, esophagus, etc. still face the challenges associated with securely closing that hole or passage upon completion of the procedure.

Consequently a need exists for devices and methods that can be employed through a patient's natural orifice for closing a passage, hole, defect, incision, etc. made or otherwise occurring through a wall of tissue such as, for example, the stomach wall, as well as those passages or holes occurring or extending through other tissues, organs, etc.

The foregoing discussion is intended only to illustrate some of the shortcomings present in the field of the invention at the time, and should not be taken as a disavowal of claim scope.

SUMMARY

In one aspect of the invention, there is provided a clip application device that may include an elongate clip magazine that has an axial clip passage therein for receiving a plurality of tissue apposition clips therein. A pair of grasper lumens may be provided in the elongate clip magazine for accommodating grasper devices therethrough to manipulate tissue adjacent to a distal end of the elongate clip magazine. The device may further include an advancement member for applying an advancement motion to the tissue apposition clips in the axial passage to cause the tissue apposition clips to move out of the axial clip passage in seriatum.

In another general aspect of various embodiments of the present invention, there is provided an adapter for installing a tissue apposition clip that has upper and lower clip arms onto tissue. In various embodiments, the adapter may comprise a body portion that is couplable to a distal end of an endoscope and is configured to releasably retain a tissue apposition clip thereon such that the upper and lower clip arms are retained in an open position to enable tissue to be drawn therebetween and thereafter be released onto the tissue upon application of an advancement force to the tissue apposition clip.

In still another general aspect of various embodiments of the present invention, there is provided a surgical method for closing an opening in a tissue wall. The method may include positioning a tissue apposition clip adjacent a distal end of an endoscope and then positioning the tissue apposition clip adjacent the opening. The method may also include grasping tissue through which the opening extends and drawing a portion of the grasped tissue into a clamping position between upper and lower clip arms of the tissue apposition clip. The method may also include advancing the tissue apposition clip onto the portion of grasped tissue.

Another general aspect of various embodiments of the present invention comprises a surgical method for closing an opening in a portion of an organ wall. The method may include the actions of positioning a tissue apposition clip adjacent a distal end of an endoscope and positioning the tissue apposition clip adjacent the opening. The method may further comprise grasping the portion of the organ wall through which the opening extends and drawing the grasped portion of the organ wall into a clamping position between upper and lower clip arms of the tissue apposition clip. In addition, the method may further comprise advancing the tissue apposition clip onto the grasped portion of the organ wall and applying at least one tissue anchor to the grasped portion or organ wall clamped within the tissue apposition clip.

In another general aspect of various embodiments of the present invention, there is a provided a surgical method for closing an opening in a tissue wall. The method may include positioning a distal end portion of a steerable overtube adjacent a portion of the opening. The method may further include inserting a flexible clip magazine into the steerable overtube, the flexible clip magazine supporting a plurality of tissue apposition clips therein such that the upper and lower clip arms thereof are supported in a spaced open position relative to each other. The flexible clip magazine may have a distal end portion received within said end of the steerable overtube such that the tissue apposition clips supported therein may be selectively discharged out through the distal end of the steerable overtube. The method may also include grasping tissue through which the opening extends and drawing a portion of the grasped tissue into a clamping position between upper and lower clip arms of a distal-most one of the tissue apposition clips supported within the distal end of the clip magazine. The method may also include advancing the distal-most tissue apposition clip onto the portion of grasped tissue.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Figure 1:
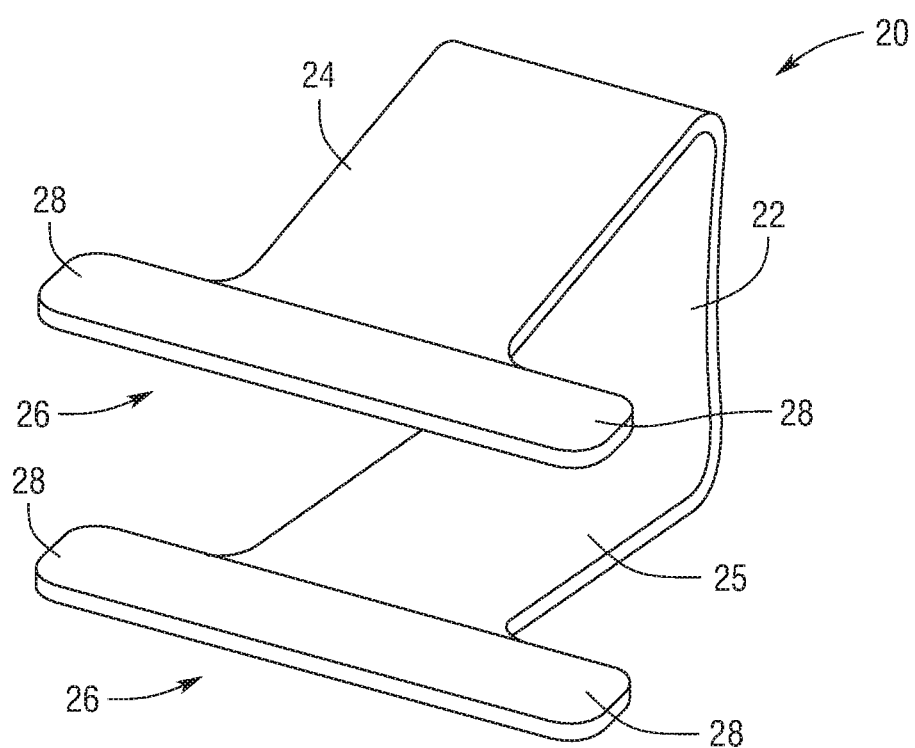
FIG. 1 is a perspective view of a tissue apposition clip embodiment of the present invention.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

It will be appreciated that the terms "proximal" and "distal" are used herein with reference to a clinician manipulating an end of the instrument 100 that protrudes out of the natural orifice. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

The present invention generally relates to devices and methods that may be used in connection with the application of tissue apposition clips for closing an opening, hole, passageway, defect, etc. extending through or occurring in a tissue wall. One example of such an opening is known as a "gastrotomy" which comprises an opening formed to gain access to the peritoneal cavity. However, as the present Detailed Description proceeds, it will become readily apparent that the various devices and methods disclosed herein may be successfully employed to apply clips to close various openings, passageways, defects, etc. in a variety of different types of tissue walls, organs, etc. without departing from the spirit and scope of the present invention. "as used herein, the term "tissue wall" is intended to at least encompass all tissues and organs within the human body or animals and includes, but is not limited to, tissue forming the abdominal wall, the stomach, the vaginal walls, the esophagus, the colon, etc. Accordingly, the various devices and methods of the present invention and their respective equivalent structures and methods should not be limited by the nature of the opening to be closed or the particular nature of the tissue through which the openings extend. Furthermore, those of ordinary skill in the art will further appreciate that the devices and methods of the various embodiments of the present invention may also be successfully employed in connection with the application of clips in open or other laparoscopic surgical procedures.

FIG. 1 depicts one embodiment of a tissue apposition clip 20 of the present invention that may be employed to clip a portion of a tissue wall such as, for example, the stomach wall or other tissue as will be discussed in further detail below. In various embodiments, the clips 20 may be fabricated from, for example, stainless steel, Nitinol, titanium or other deformable materials that are implantable within the body and are compatible with that type of environment. As can be seen in FIG. 1, a tissue apposition clip 20 may have a base portion 22 that separates an upper clip arm 24 and a lower clip arm 25 that extend from the base in general confronting relationship to each other. The distal end portions 26 of each clip arm 24, 25 are generally biased towards each other in a "clamping position" or orientation. Each distal end portion 26 may also be formed with two laterally extending protrusions 28, the purpose of which will be discussed below. While the clip 20 depicted in FIG. 1 comprises a preferred tissue apposition clip configuration, other tissue apposition clip configurations could also be employed with the clip application device 100 described below.

In various embodiments, a clip application device 100 of various embodiments of the present invention may be used in connection with a steerable overtube 200. Those of ordinary skill in the art will appreciate that the clip application device 100 may be used in connection with a variety of different steerable overtube arrangements. For example, the steerable overtube 200 may comprise a steerable overtube of the type disclosed in U.S. patent application Ser. No. 11/981,134, filed Oct. 31, 2007, entitled "Endoscopic Overtubes" to Gregory J. Bakos et al., the disclosure of which is herein incorporated by reference in its entirety. Still other overtubes may be employed such as those disclosed in U.S. Pat. No. 5,325,845 to Adair, the disclosure of which is herein incorporated by reference in its entirety. In other embodiments, a steerable overtube of the various types disclosed in commonly owned U.S. patent application Ser. No. 12/172,782, Entitled "Endoscopic Translumenal Articulatable Steerable Overtube" to Gregory J. Bakos et al., filed on Jul. 14, 2008, now U.S. Pat. No. 8,262,563, and which is hereby incorporated by reference in its entirety, may be successfully employed. In other embodiments, a non-steerable overtube could conceivably be employed, depending upon the application.

Figure 2:
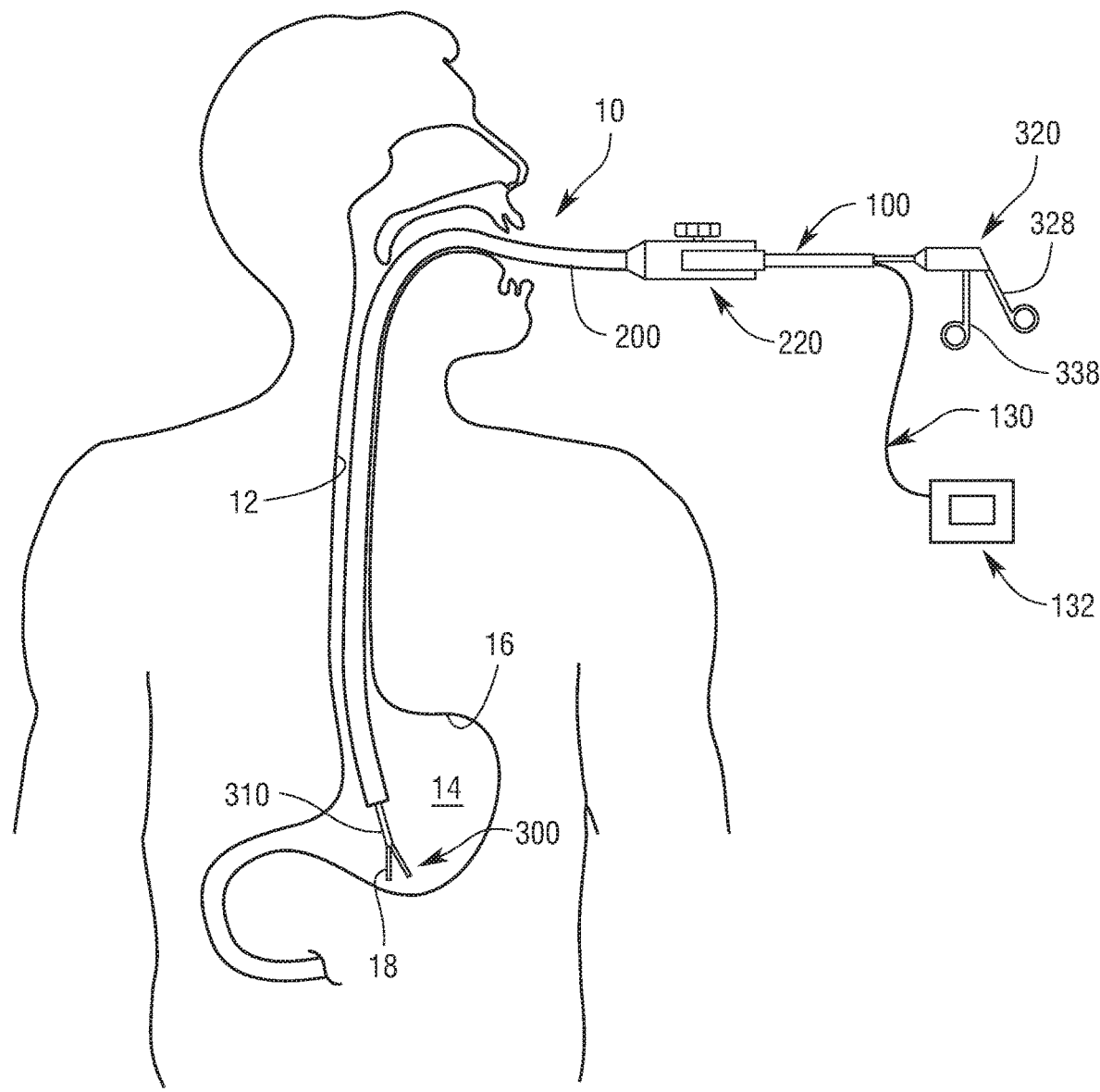
FIG. 2 is diagrammatic view of use of a clip application device embodiment of the present invention inserted through a natural orifice (mouth) of a patient.
Figure 3:
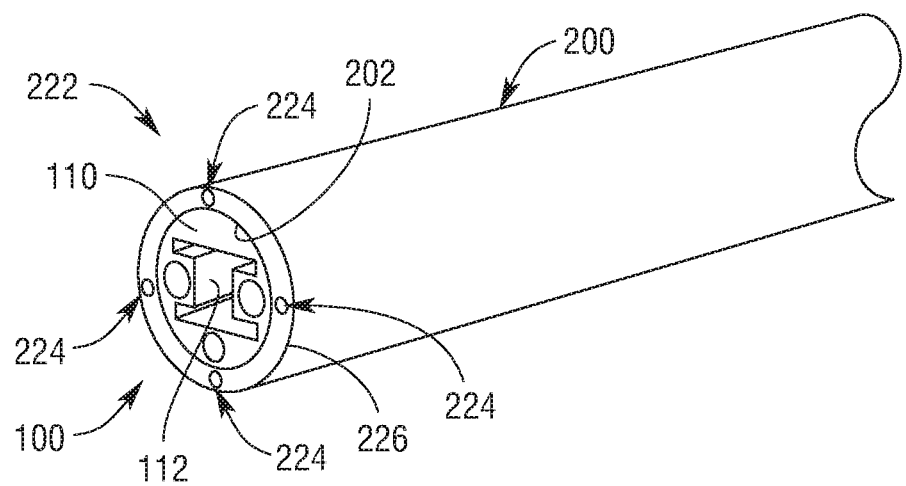
FIG. 3 is a perspective view of portion of a clip application device of the present invention.
Figure 4:
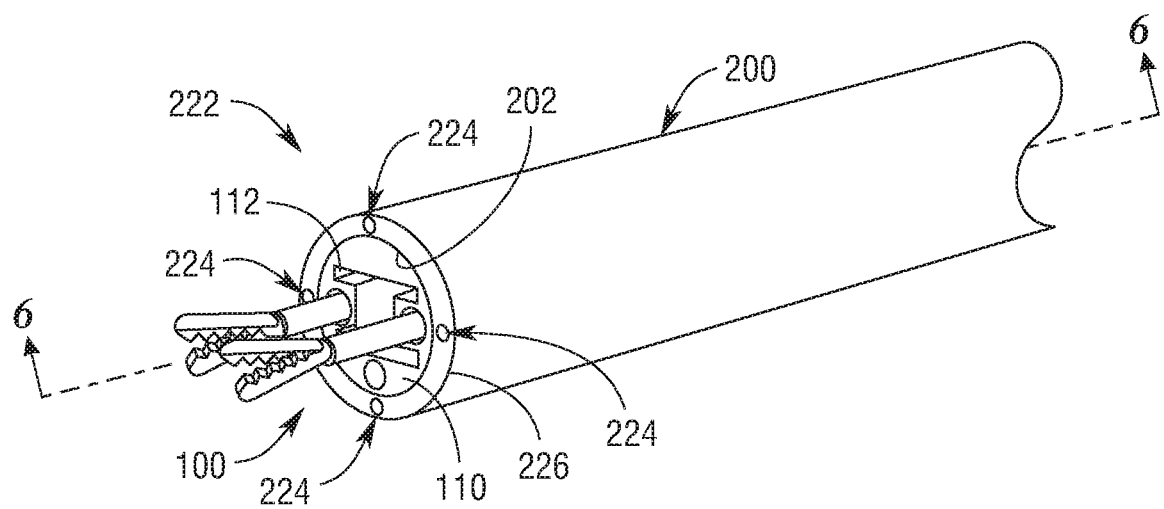
FIG. 4 is another perspective view of a portion of the clip application device of the present invention with graspers extending out of the distal end thereof.

As can be seen in FIG. 2, one version of the steerable overtube 200 may interface with an actuator 220 that is used to articulate the distal end portion 222 of the overtube 200. The steerable overtube 200 has a central lumen 202 through which various endoscopic surgical tool and instruments may pass. See FIGS. 3 and 4. The actuator 220 may be used to selectively apply tension to cables or tension members 224 that extend through the wall 226 of the overtube 200 to draw the distal end portion 222 thereof in a desired direction.

Although, as discussed above, the various embodiments of the present invention may be successfully employed to apply clips to and/or close a hole, passageway, defect, etc. in a variety of different tissue walls and organs, one example in which the clip application 100 has particular utility is the closure of a gastrotomy created through the abdominal wall to gain access to the peritoneal cavity. FIG. 2 illustrates one method of deploying an embodiment of the clip application device 100 of the present invention through a natural orifice to close a gastrotomy. As shown in FIG. 2, the steerable overtube 200 may be inserted through the mouth 10 and esophagus 12 into the stomach 14, for example, to enable the surgeon to create a gastrotomy through a portion of the stomach wall. The gastrotomy may be accomplished utilizing various surgical instruments that are operated through the overtube. Once the gastrotomy has been created and the other surgical procedures have been completed, the surgical tools that have been employed up to this point may be removed from the overtube 200 and a clip application device 100 of the present invention may be inserted through the overtube 200 and into the stomach 14 as shown.

Figure 5:
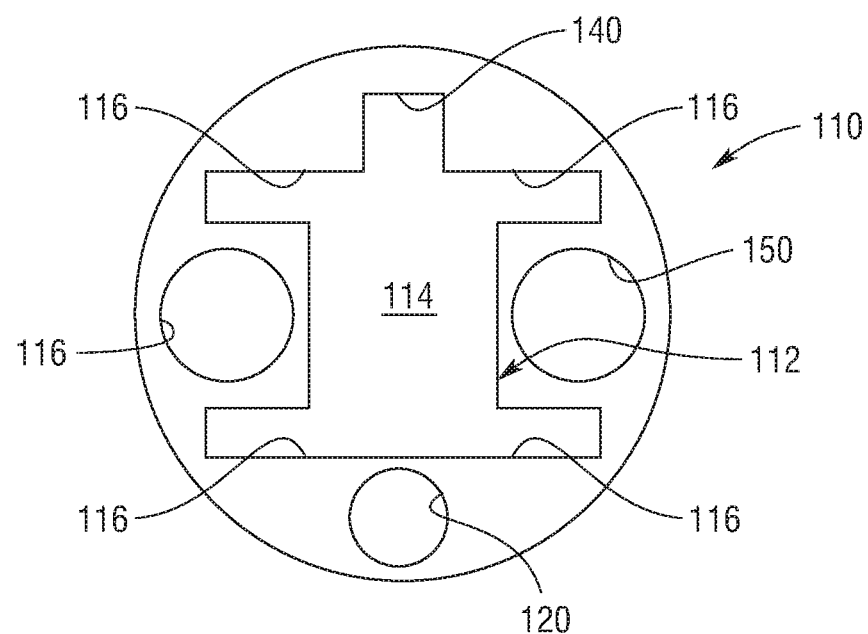
FIG. 5 is an end view of a clip magazine embodiment of the present invention.
Figure 6:
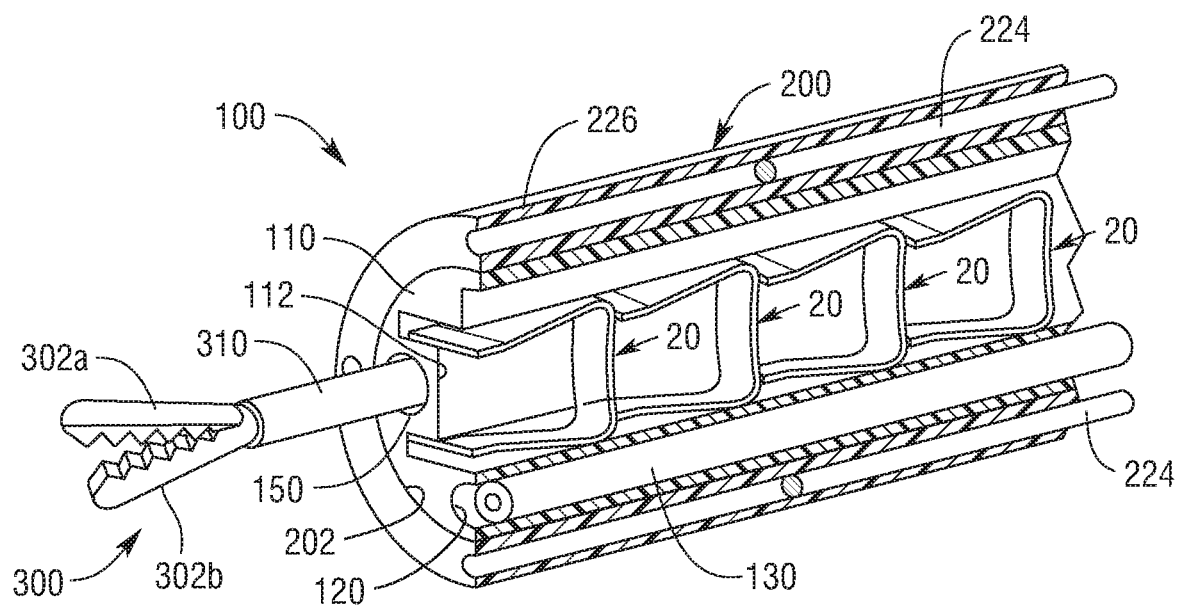
FIG. 6 is a cross-sectional view of the clip application device of FIG. 4 taken along line 6-6 in FIG. 4.

FIGS. 3-6 and 8-10 illustrate one embodiment of the clip application device 100 of the present invention. As can be seen in those Figures, the clip application device 100 may include an elongated clip magazine 110 that is sized to extend through the central lumen 202 in the steerable overtube 200. In various embodiments, the clip magazine 110 may be extruded or otherwise formed from polyurethane, silicone, etc. such that the clip magazine 110 may flex or otherwise conform to the steerable overtube 200. The clip magazine 110 may be formed with a centrally disposed axial clip passage 112 that is shaped to movably accommodate at least one and preferably a series, of clips 20 as illustrated in FIG. 6. As can be seen in FIG. 5, the axial clip passage 112 may have a central passage portion 114 and four leg passage segments 116 that protrude laterally from the central passage portion to accommodate the clip arms of the clips 20. As can be seen in FIG. 6, the leg passage segments 116 may serve to support the upper clip arm 24 and the lower clip arm 25 in a spaced open position relative to each other to enable the clip 20 to be installed over tissue as will be discussed in further detail below.

The clip magazine 110 may further have a channel 120 formed therein for operably supporting a conventional endoscopic video camera 130 that communicates with a video display unit 132 that can be viewed by the surgeon during the operation. See FIG. 2. In addition, an advancement channel 140 may be provided in the clip magazine 110 for accommodating various mechanisms for serially advancing the clips 20 out of the distal end of the clip magazine 110.

Figure 7:
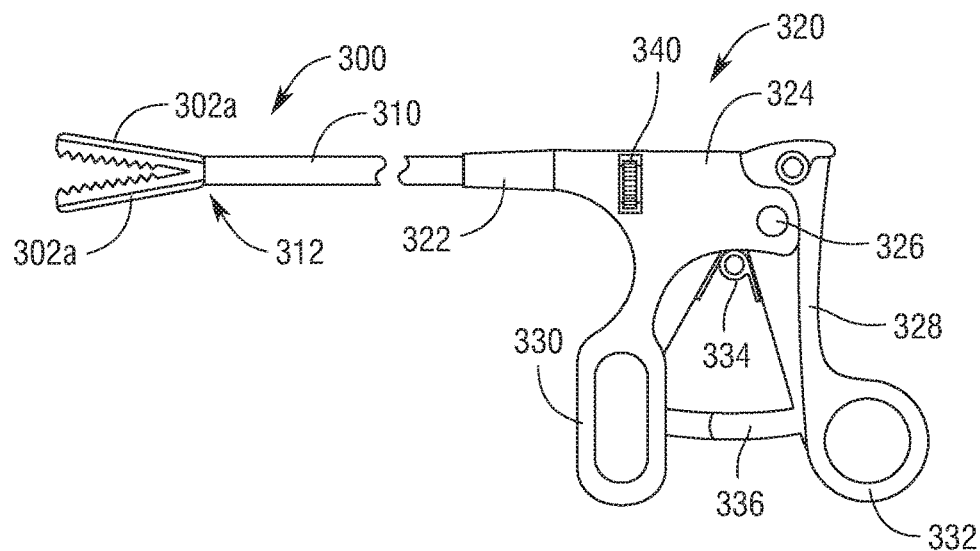
FIG. 7 is a side view of a grasper embodiment.

Also in various embodiments, the clip magazine 110 may be provided with at least one and preferably two lumens 150 for operably accommodating graspers 300. A variety of different known graspers may be employed without departing from the spirit and scope of the present invention. In general, a grasper 300 may include a pair of opposed jaws 302a, 302b that are operably located at a distal end 312 of an elongate shaft 310. The proximal end of elongate shaft 310 may be coupled to a handle assembly 320 at collar 322. The handle assembly 320 may further include a fixed handle 324 that is pivotally engaged at point 326 to a moving handle 328. Handles 324, 328 may have grasping loops 330, 332 attached thereto for the convenient insertion of fingers or a thumb therein. The handle assembly 320 depicted in FIG. 7 includes a spring clip 334 and ratchet 336 as two means of providing bias to handles 330, 332 such that jaws 302a, 302b are urged in a closed position. Though both are pictured here together (for convenience), usually one or the other is used as means to bias jaws shut. The grasper 300 may further have an adjustable knob 340 which causes shaft 310 and therefore jaws 302a, 302b to rotate with respect to fixed handle 330. The jaws 302a, 302b may be opened and closed by manipulating the handles 324, 328. A variety of different graspers and grasper jaw configurations are known and may successfully employed in connection with various embodiments of the present invention. Accordingly, the protections afforded to the various embodiments of the subject invention and their equivalent structures should not be limited to the specific grasper configuration depicted in FIG. 7.

To use the device 100, the graspers 300 are inserted into their respective lumens 150 in the clip magazine 110 such that the jaws 302a, 302b protrude out through the distal end of the clip magazine 110 as shown in FIG. 5. At least one, and preferably a plurality of, clips 20 are inserted in seriatum into the axial clip passage 112 of the clip magazine 110 and may be advanced therein in the distal direction "DD" by an advancement member 350 that may be inserted into the advancement channel 140 in the clip magazine 110. See FIG. 6. While a variety of different clip advancement mechanisms could be used, the clip advancement member 350 may have a distal end 352 that has a notched portion 354 therein for engaging the proximal-most clip 20 to apply a pushing force thereto in the distal direction "DD".

Figure 8:
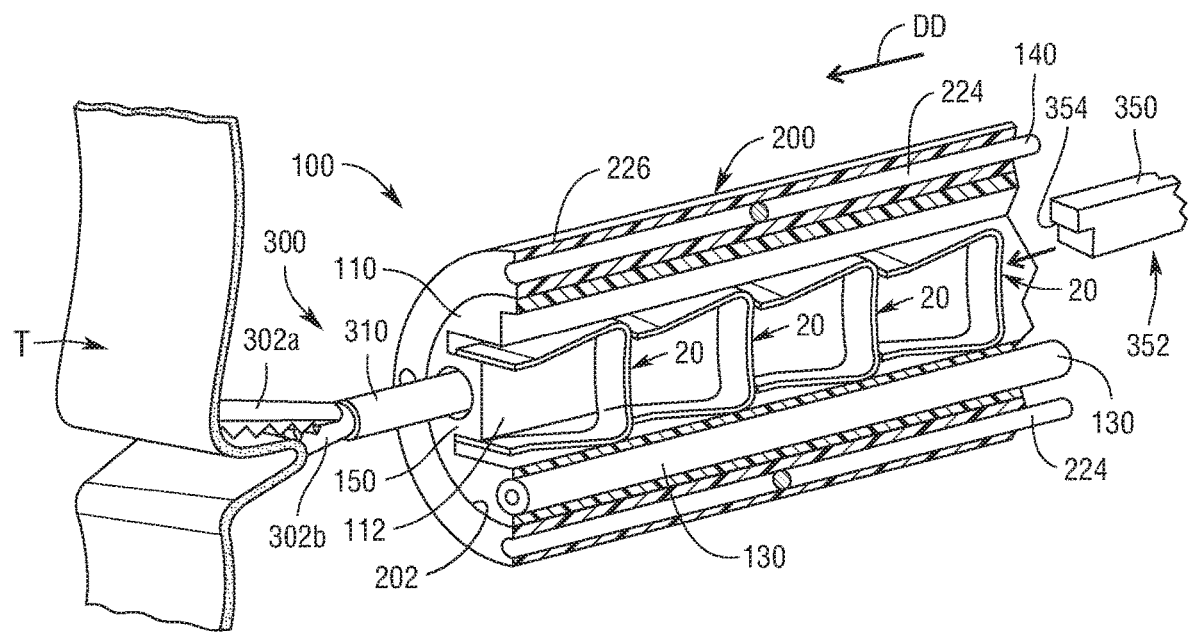
FIG. 8 is another cross-sectional view of the clip application device embodiment of FIG. 6 with one of the graspers thereof gripping tissue.
Figure 9:
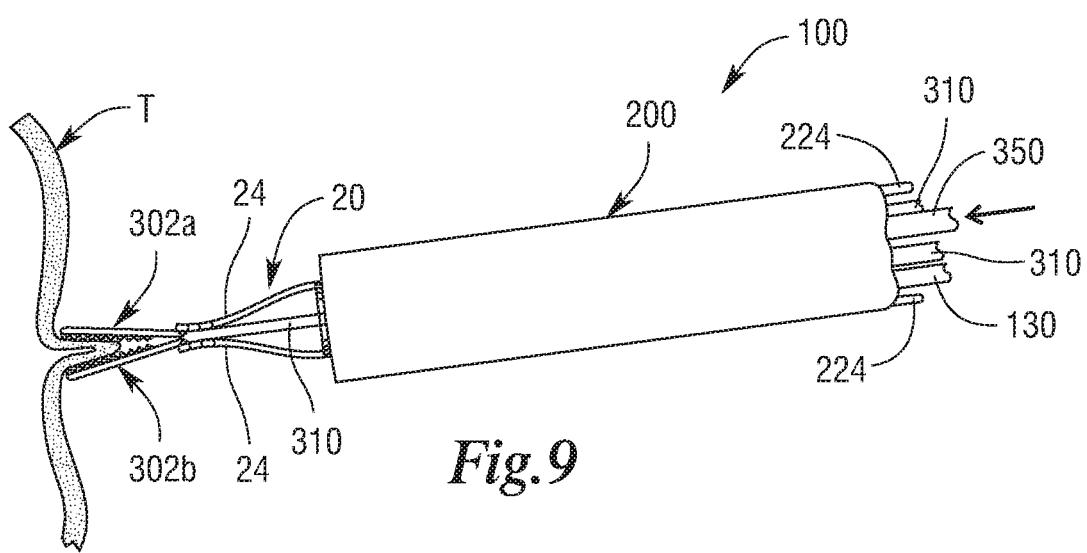
FIG. 9 is a partial side view of the clip application device of FIG. 8.
Figure 10:
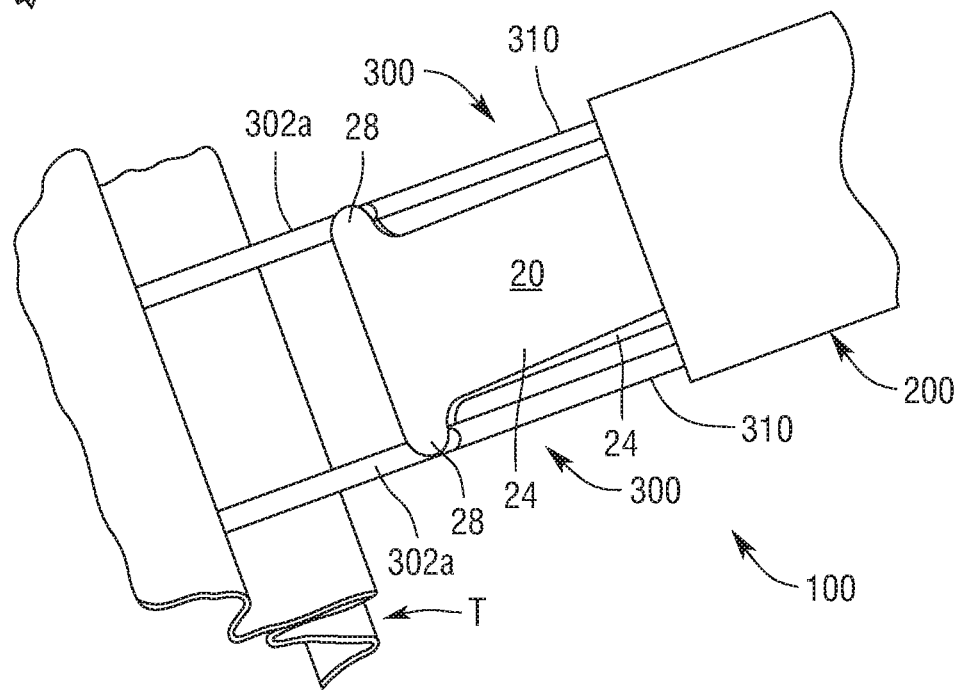
FIG. 10 is a partial perspective view of a portion of the clip applier applying a clip to tissue.
Figure 11:
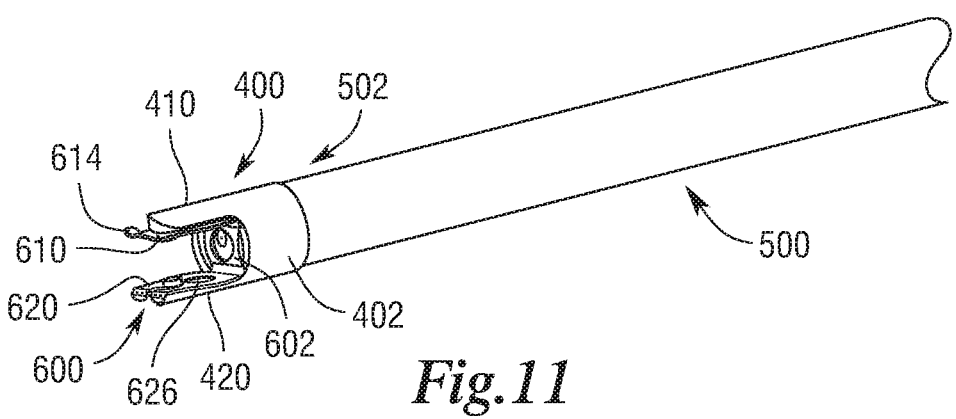
FIG. 11 is a perspective view of another clip application device coupled to an endoscope.

When the surgeon desires to apply the clips 20 to the gastrotomy site, the distal end of the clip application device 100 is inserted in through the patient's mouth 10 or other natural orifice such that the graspers 300 may be extended out of the distal end of the clip magazine 110 to grasp the tissue "T" as shown in FIGS. 8-10. Once the tissue "T" has been acquired by the graspers 300 (as observed by the surgeon by means of the camera 130), the surgeon may then pull the grasped tissue proximally between the spaced upper clip arm 24 and lower clip arm 25 of the distal-most clip 20. The surgeon may also begin to apply an advancement force to the proximal-most clip 20 by inserting the advancement member 350 into the advancement channel 140. The application of such advancement force to the proximal-most clip 20 causes the entire series of clips 20 to move proximally in the clip magazine 110 until the distal-most clip 20 is advanced out of the distal end of the clip magazine 110. As can be seen in FIG. 10, the laterally extending protrusions 28 enable the clip 20 to ride up the elongate shaft 310 and the jaws 302a, 302b of the graspers 300 to retain the upper and lower clip arms 24, 25 in the spaced open position. The clip 20 continues to be advanced until it engages the tissue "T" and disengages the ends of the grasper jaws 302a, 302b. At that point, the clip 20 is holding the tissue folds together and additional clips 20 may be applied in a similar manner or the device 100 may be withdrawn from the patient.

Those of ordinary skill in the art will understand that, although intended to be permanent, these clips 20 may also be designed to slough off intentionally from the clipped tissue to enable the clips to be passed naturally. Although not intended, it is also possible that the clips may come loose from the clipped tissue. In either case, however, it may be desirable for the clips 20 to be sized to enable the clip to pass naturally from the patient without causing harm to the patient. For example, the clips 20 may have smooth rounded edges without significant catch points that could hinder safe passage of the clips 20 from the body.

Figure 12:
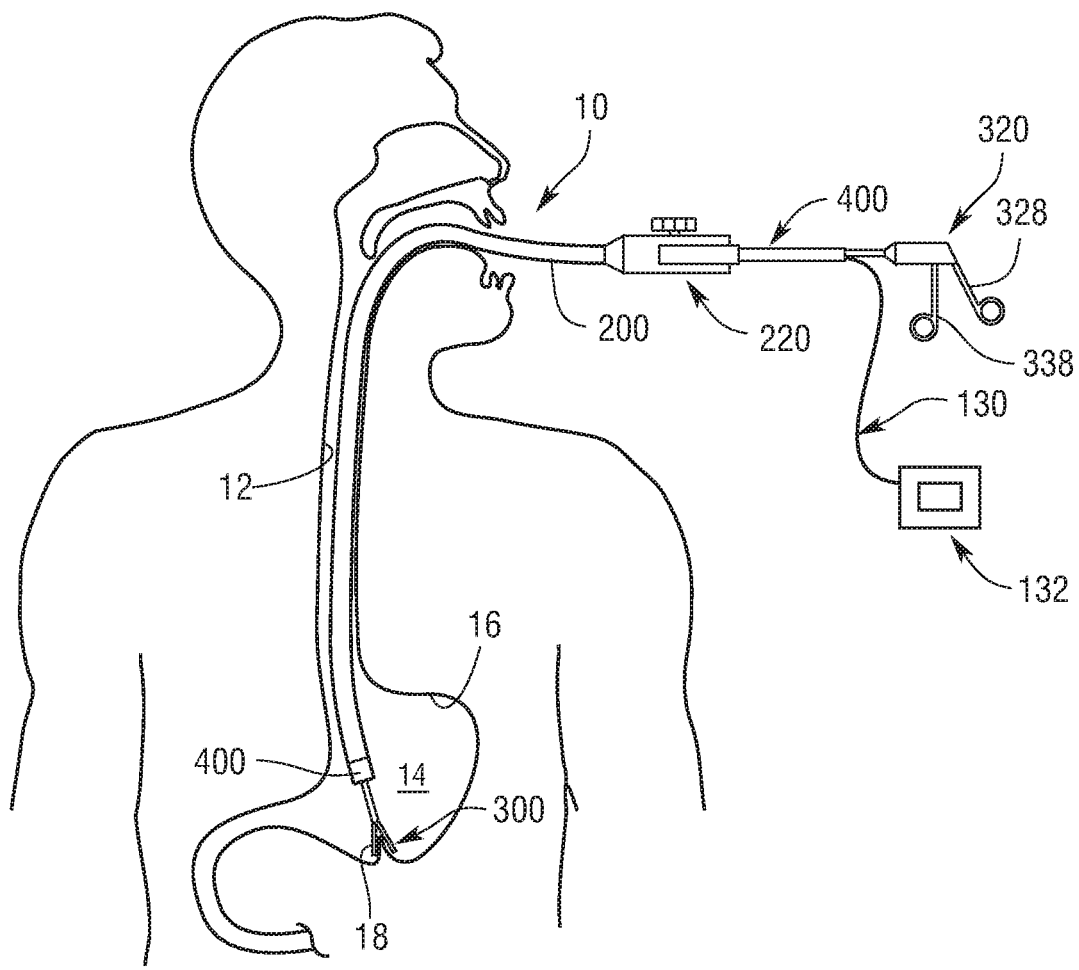
FIG. 12 is a diagrammatic view of use of another clip application device embodiment of the present invention inserted through a natural orifice (mouth) of a patient.
Figure 13:
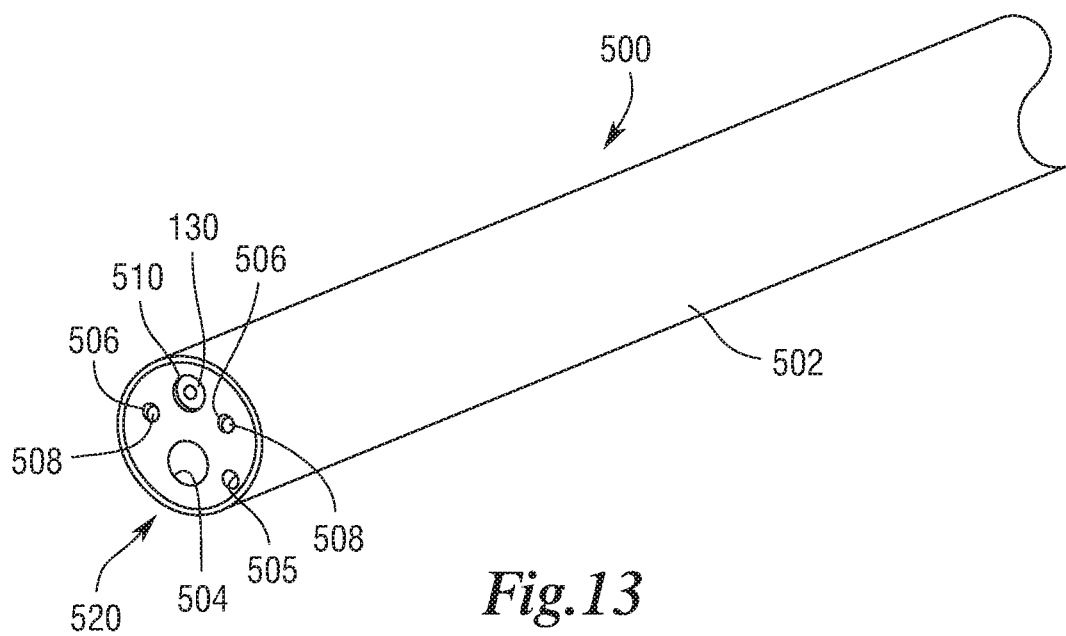
FIG. 13 is a perspective view of an endoscope with which a clip adapter embodiment of the present invention may be used.

FIGS. 11-15 illustrate a clip dispensing adapter 400 that may be used with a conventional endoscope 500. As can be seen in FIG. 12, the endoscope 500 may be passed through the steerable overtube 200 and otherwise guided thereby to the site 18 of the opening in the stomach 14. One form of endoscope 500 that may be employed is illustrated in FIG. 13. As can be seen in that Figure, the endoscope 500 may have an elongate, relatively flexible body 502 that has a working channel or lumen 504 extending therethrough. In addition, the endoscope body 502 may have two or more channels 506 that operably support light bundles 508 therein as well as a camera channel 510 for operably accommodating a video camera 130 therein.

Figure 15:
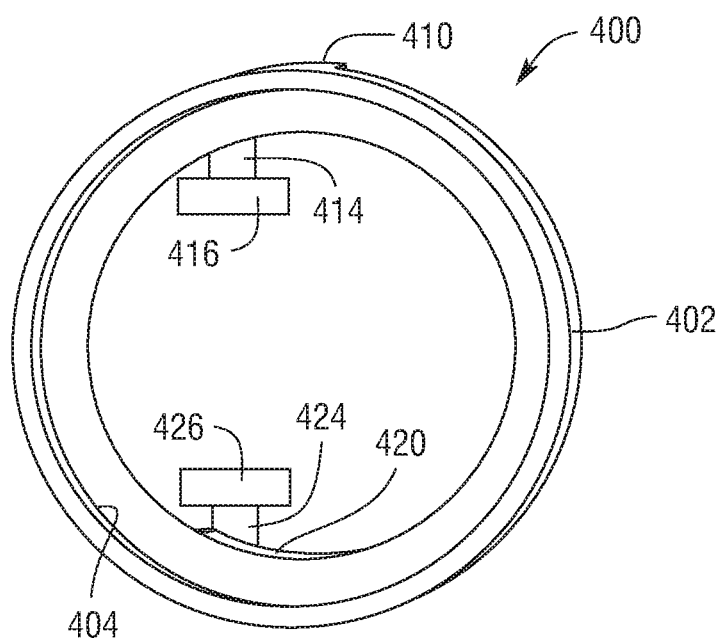
FIG. 15 is an end view of the clip adapter embodiment of the FIG. 14.
Figure 16:
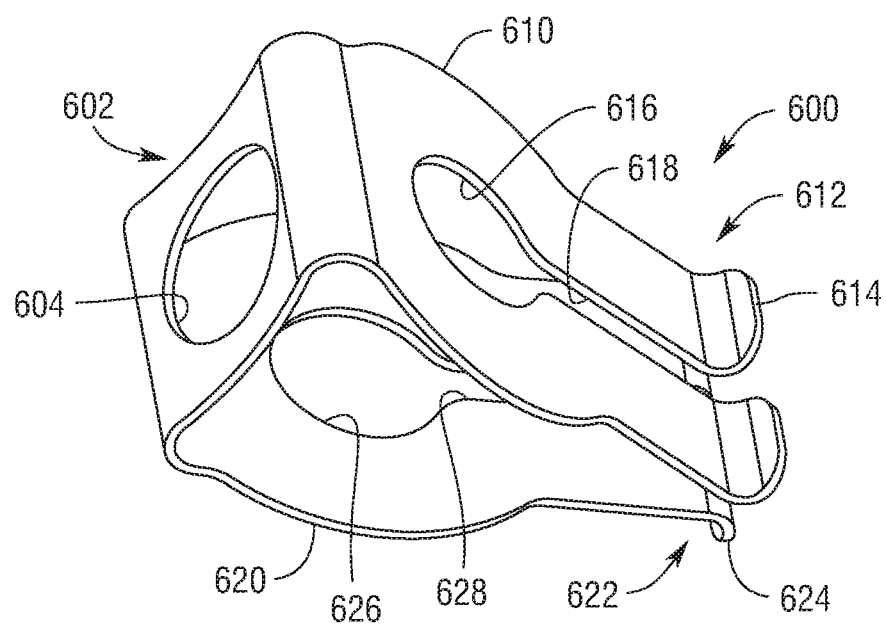
FIG. 16 is a top perspective view of another a tissue apposition clip embodiment of the present invention.

On embodiment of a clip dispensing adapter 400 is depicted in further detail in FIGS. 15 and 16. As can be seen in those Figures, the clip dispensing adapter 400 has a body portion 402 that is sized to fit over the distal end 520 of the endoscope 500. In various embodiments, the body portion 402 has an endoscope-receiving cavity 404 therein that may have an inner diameter that is sized relative to the outer diameter of the distal end 520 of the endoscope 500 such that a frictional fit is established therebetween when the adapter 400 is installed onto the distal end 520. See FIG. 15. For example, in such embodiment, the adapter may be fabricated from, for example, stainless steel, polycarbonate, aluminum, etc. In other embodiments, the adapter 400 may be affixed to the distal end 520 of the endoscope 500 by an appropriate adhesive. In still other embodiments, the adapter 400 may be fabricated from a somewhat elastic material such as, for example, silicone, polyurethane, etc. to enable the adapter 400 to be slid over the distal end 520 of the endoscope 500 and retained thereon. In yet other embodiments, the adapter 400 and the distal end 520 of the endoscope 500 may be configured with threads, bayonet-type connections, ratchet connections, etc. to enable the adapter 400 to be removed from the endoscope 500 if so desired. In other embodiments, the adapter 400 may be permanently affixed or otherwise integrally formed into the distal end 520 of the endoscope 500.

Figure 14:
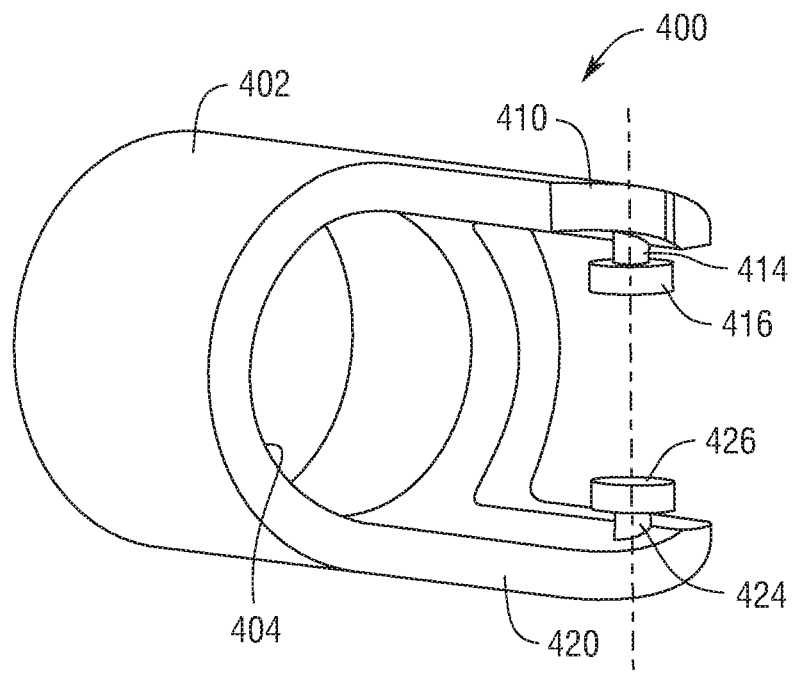
FIG. 14 is a perspective view of a clip adapter embodiment of the present invention.
Figure 17:
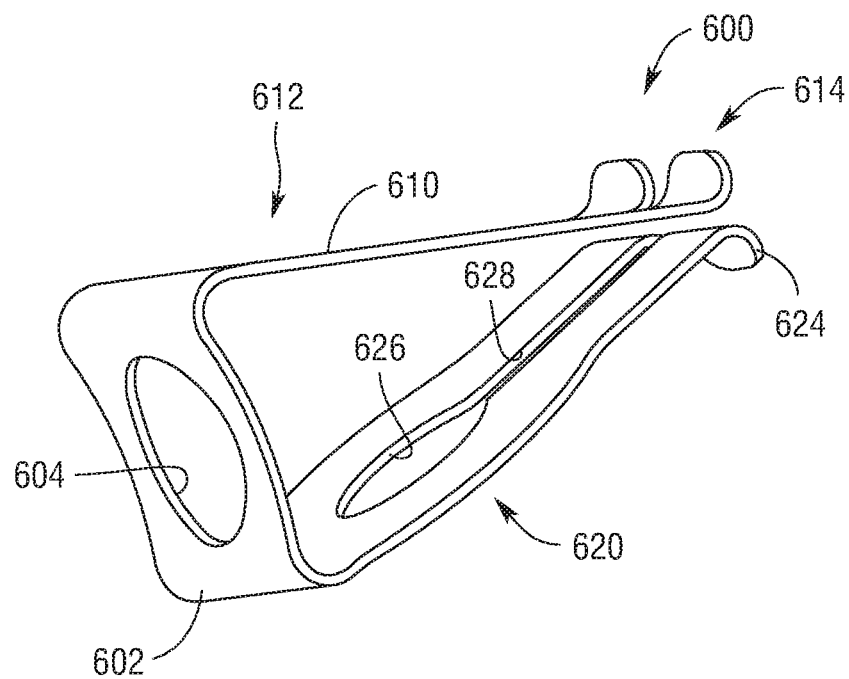
FIG. 17 is a side perspective view of the tissue apposition clip of FIG. 16.

As can be seen in FIGS. 14 and 15, the adapter 400 may further include an upper support arm 410 and a lower support arm 420 that protrude outward from the distal end of the body portion 402. The support arms 410, 420 are spaced from each other to receive a tissue apposition clip 600 therebetween. One example of a tissue apposition clip 600 that may be employed is depicted in FIGS. 16 and 17. In various embodiments, the clip 600 may be fabricated from, for example, stainless steel, Nitinol, titanium, hard plastic, etc. and have a base portion 602 that separates an upper clip arm 610 and a lower clip arm 620 that extend from the base in general confronting relationship to each other. The distal end portion 612 of the upper clip arm 610 and the distal end 622 of the lower clip arm 620 are generally biased towards each other in a "clamping orientation". The distal end 612 may have a folded end portion 614 and the distal end 622 may have a folded end portion 624. The end portions 614 and 624 help to facilitate installation of the clip 600 as it is advanced over folded tissue. In various embodiments, the upper clip arm 610 may have an upper opening 616 therein and an upper slot 618 that extends from the upper opening 616 through the distal end portion 612. Similarly, the lower clip arm 620 has a lower opening 626 and a lower slot 628 extending from the lower opening 626.

Figure 18:
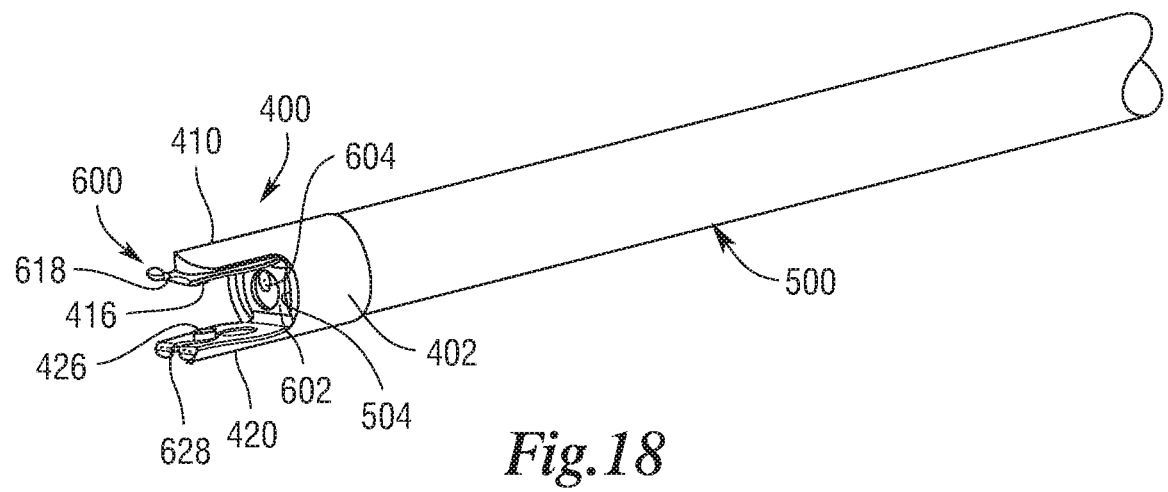
FIG. 18 is a perspective view of a clip dispenser adapter embodiment on an endoscope.
Figure 19:
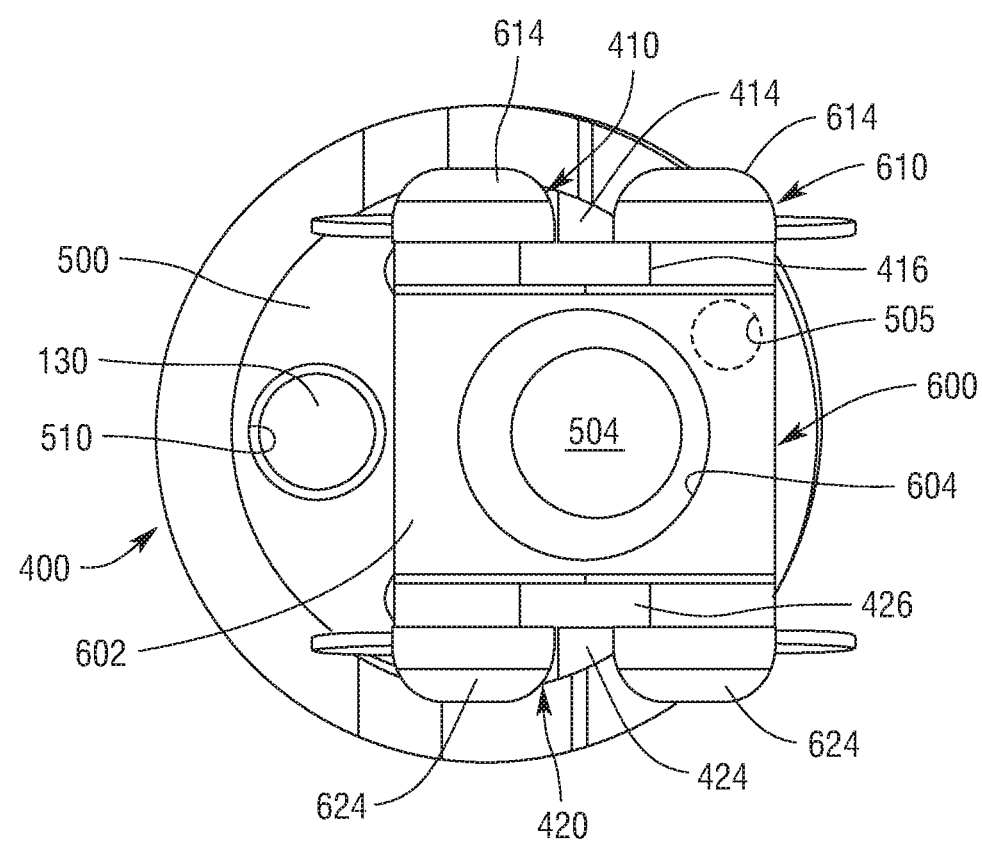
FIG. 19 is an end view of the clip dispenser adapter embodiment and endoscope of FIG. 18 with a tissue apposition clip installed therein.

FIGS. 18-21 illustrate use of the tissue apposition clip 600 with the adapter 400. For example, as can be seen in FIG. 18, the tissue apposition clip 600 may be positioned between the upper support arm 410 and the lower support arm 420. Upper support arm 410 may have a downwardly extending post 414 that has retainer lug 416 formed thereon that is sized to be received in the upper opening 616 in the upper clip arm 610. Similarly, the lower support arm 420 may have an upwardly extending post 424 that has a retainer lug 426 thereon that is sized to be received in the lower opening 626 in the lower clip arm 620. Thus, to install the tissue apposition clip 600 onto the adapter 400, the tissue apposition clip 600 is oriented between the upper support arm 410 and the lower support arm 420 such that the upper retainer lug 414 extends into the opening 616 and the lower retainer lug 424 extends into the opening 626. The tissue apposition clip 600 is then moved distally such that the post 414 is received in the upper slot 618 and the lower post 424 is received in the lower slot 628 of the clip 600 in the "open" position shown in FIG. 18.

Figure 20:
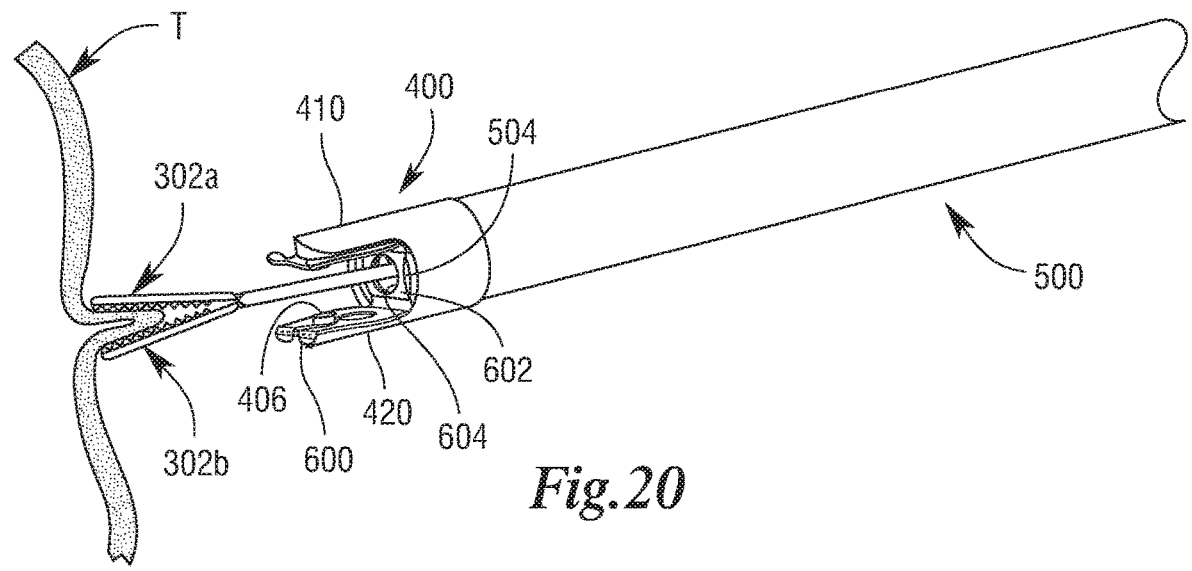
FIG. 20 is a side perspective view of the clip dispenser adapter embodiment of FIG. 19 with a grasper protruding out through the distal end thereof to grasp tissue.
Figure 21:
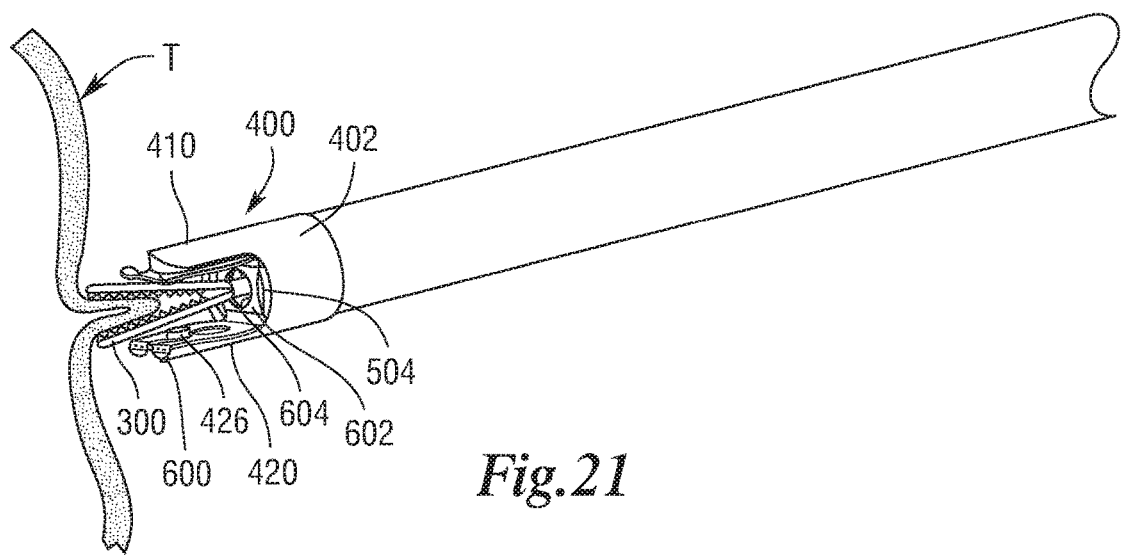
FIG. 21 is another perspective view of the clip dispenser adapter embodiment of FIG. 20 illustrating the grasper pulling tissue in between the clip arms of a clip installed therein.

As can be seen in FIGS. 18-21, the base portion 602 of the clip 600 may have a hole 604 therethrough that is aligned with a working channel 504 in the endoscope 500 when the clip 600 is installed onto the adapter 400. This alignment of hole 604 with the working channel 504 enables a grasper 300 to be inserted therethrough to grasp the tissue "T" as shown in FIGS. 20 and 21. Once the surgeon has grasped the target tissue "T" with the grasper 300 in the manner described above and as illustrated in FIG. 20, the surgeon can then pull the grasper 300 and tissue "T" proximally into the open tissue apposition clip 600 as shown in FIG. 21. While the surgeon is pulling the grasper 300 and tissue "T" proximally, the tissue apposition clip 600 may be pushed onto the tissue by advancing an advancement member (rod, bar, other surgical instrument, etc.) through the working channel 505 to contact the clip base 602 and push it distally onto the tissue "T". When the tissue apposition clip 600 is pushed distally, the lugs 416, 426 will enter the holes 616, 626, respectively to enable the tissue apposition clip to enable the tissue apposition clip 600 to disengage from the adapter 400 and remain on the tissue "T" as the grasper 300 is withdrawn through the hole 604 and working channel 504.

Figure 22:
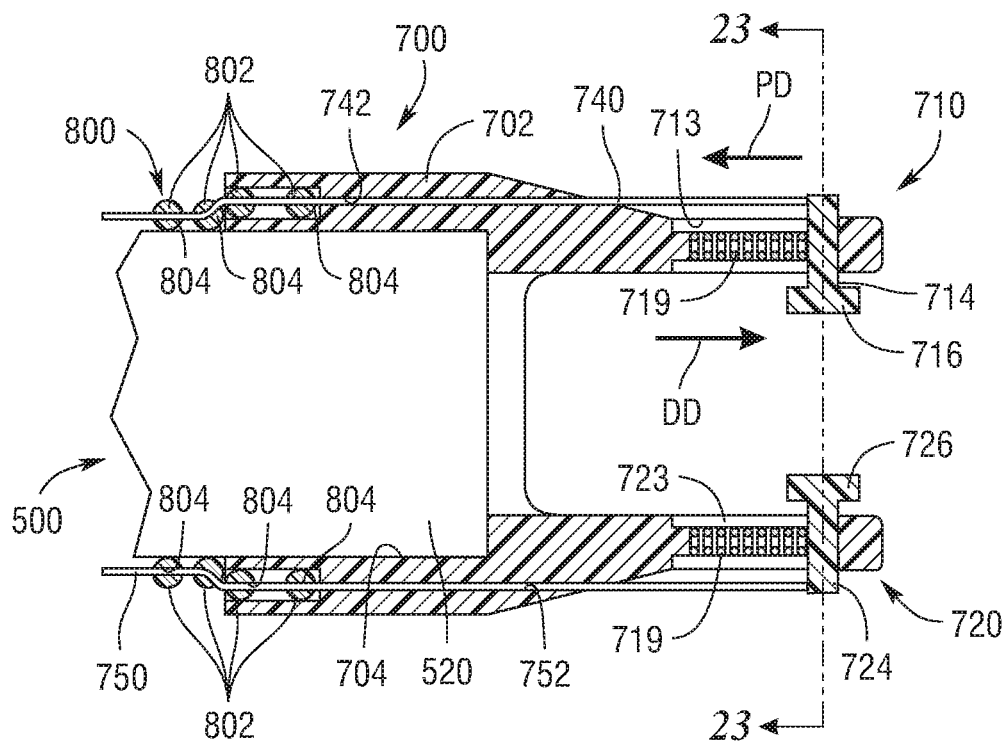
FIG. 22 is a partial cross-sectional view of yet another embodiment of a clip dispenser adapter embodiment of the present invention attached to the distal end of an endoscope.
Figure 23:
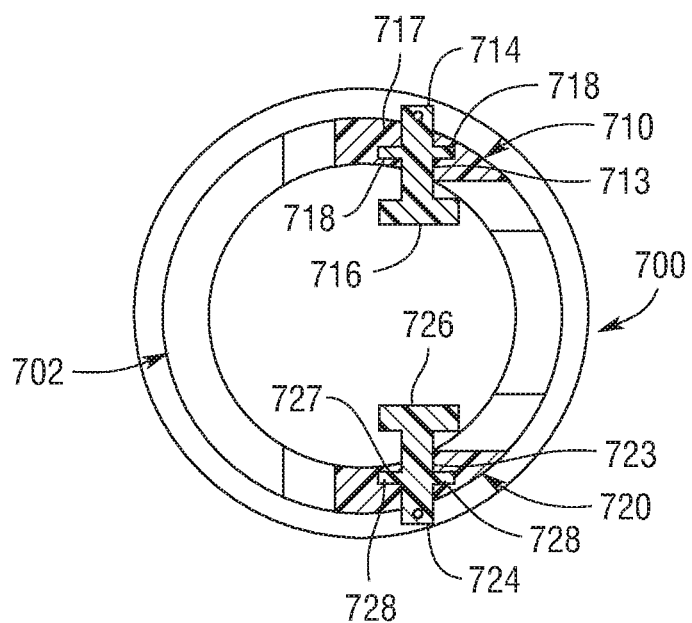
FIG. 23 is a partial cross-sectional end view of the clip dispenser adapter embodiment of FIG. 22.

FIGS. 22 and 23 illustrate another clip dispensing adapter 700 that may be effectively used in connection with the tissue apposition clips 600 described above. As can be seen in those Figures, the clip dispensing adapter 700 has a body portion 702 that is sized to fit over the distal end 520 of the endoscope 500. In various embodiments, the body portion 702 may have an endoscope-receiving cavity 704 therein that may have an inner diameter that is sized relative to the outer diameter of the distal end 520 of the endoscope 500 such that a frictional fit is established therebetween when the adapter 400 is installed onto the distal end 520. For example, in such embodiment, the adapter may be fabricated from stainless steel, aluminum, hard plastic, etc. In other embodiments, the adapter 700 may be affixed to the distal end 520 of the endoscope 500 by an appropriate adhesive. In still other embodiments, the adapter 700 may be fabricated from a somewhat elastic material such as, for example, silicone, polyurethane, elastomer, etc. to enable the adapter 700 to be slid over the distal end 520 of the endoscope 500 and retained thereon. In yet other embodiments, the adapter 700 and the distal end 520 of the endoscope 500 may be configured with threads, bayonet-type connections, ratchet connections, etc. to enable the adapter 700 to be removed from the endoscope 500 if so desired. In other embodiments, the adapter 700 may be permanently affixed or otherwise integrally formed into the distal end 520 of the endoscope 500.

Figure 24:
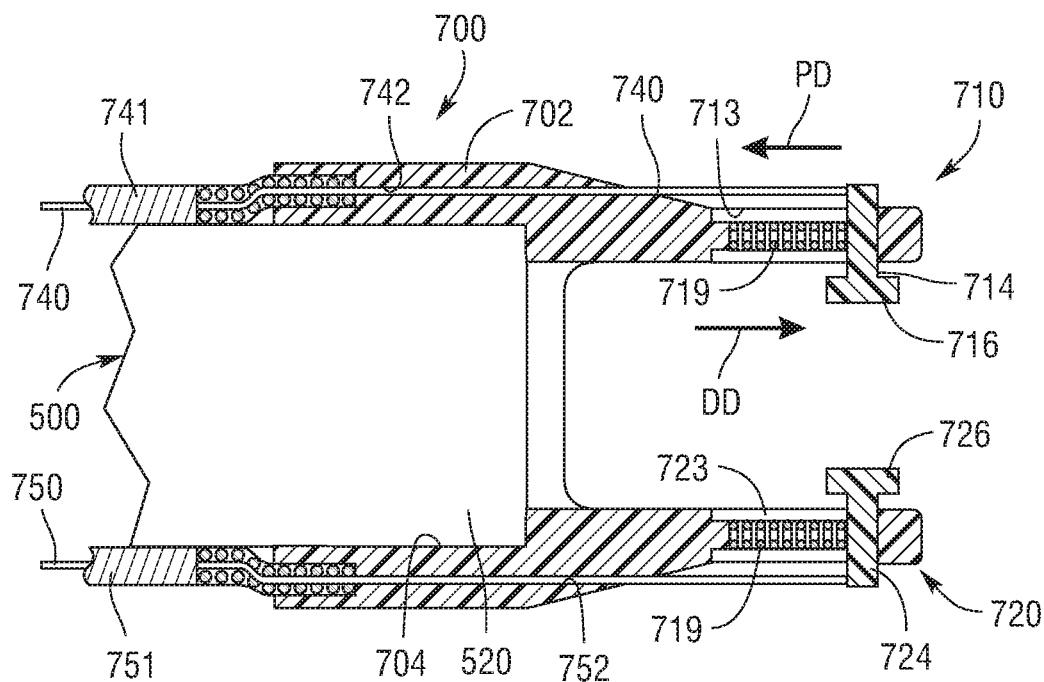
FIG. 24 is a partial cross-sectional view of yet another embodiment of a clip dispenser adapter embodiment of the present invention attached to the distal end of an endoscope.

As can be seen in FIGS. 22 and 23, the adapter 700 may further include an upper support arm 710 and a lower support arm 720 that protrude outward from the distal end of the body portion 702. The support arms 710, 720 are spaced from each other to receive a tissue apposition clip 600 therebetween. Upper support arm 410 has a downwardly extending movable post 714 that has retainer lug 716 formed thereon that is sized to be received in the upper opening 616 in the upper clip arm 610. As can be seen in FIGS. 22 and 23, the movable post 714 is movably supported within a slot 713 in the upper support arm 710. In various embodiments, the movable post 714 may have laterally protruding fins 718 that are received in corresponding slots 717 in the upper support arm 710 such that the movable support post 714 can move in the proximal direction "PD" and the distal direction "DD". The movable support arm 714 is biased into a retention position shown in FIG. 23 by an upper biasing member 719. Similarly, the lower support arm 720 has an upwardly movable post 724 that has a retainer lug 726 thereon that is sized to be received in the lower opening 626 in the lower clip arm 620. As can be seen in FIGS. 23 and 24, the movable post 724 is movably supported within a slot 723 in the lower support arm 720. In various embodiments, the movable post 724 may have laterally protruding fins 728 that are received in corresponding slots 727 in the lower support arm 720 such that the movable support post 724 can move in the proximal direction "PD" and the distal direction "DD". The movable support arm 724 is biased into a retention position shown in FIG. 23 by a lower biasing member 729.

As can also be seen in FIG. 22, an upper retraction cable 740 extends through a passage 742 in the adapter 700 and is affixed to the upper movable support post 714 and a lower retraction cable 750 extends through a passage 752 in the adapter 700 and is affixed to the lower movable support post 724. The upper and lower retraction cables 740, 750 extend through corresponding passages in a flexible tube 800 that extends over the endoscope 500. In various embodiments, the tube 800 may include a helical wound coil of material that can flex with the endoscope 500 and is substantially coextensive therewith. For example, the flexible tube 800 may be fabricated from stainless steel wire. The various coils 802 of the flexible tube may be provided with corresponding holes 804 through which the retraction cables 740, 750 extend. The distal end 810 of the flexible tube 800 may extend into a retention cavity 760 formed in the proximal end of the adapter body 702 and be attached thereto, by pins, screws, adhesive, etc. The flexible tube 800 serves to guide the retraction cables 740, 750 along the endoscope 500 and out through the patient's mouth or other natural orifice. Pulling on the retraction cable 740 in the proximal direction "PD, causes the upper movable post 714 to move in the proximal direction. Likewise, pulling on the retraction cable 750 in the proximal direction "PD" causes the lower movable post 724 to move in the proximal direction. In alternative embodiments, each cable 740, 750 could extend through its own dedicated flexible coil pipe 741, 751, respectively, which would extend alongside of the endoscope. See FIG. 24.

To install the clip 600 onto the adapter 700, the clip 600 is oriented between the upper support arm 710 and the lower support arm 720. Once positioned in the adapter 700, the surgeon may then apply retraction forces to the retraction cables 740, 750 in the proximal direction such that the upper retainer lug 716 extends into the opening 616 and the lower retainer lug 726 extends into the opening 626 in the clip 600. The surgeon may then release the retraction cables 740, 750 and the upper biasing member 719 biases the upper movable post 714 into the retention position and the lower biasing member 729 biases the lower movable post 724 into the retention position to retain the clip 600 in position between the upper and lower support arms 710, 720. The surgeon may then insert a grasper (not shown) through the working channel in the endoscope 500 and through the clip 600 to grasp the tissue in the manner described above and then pull the tissue into a position between the upper and lower clip arms 610, 620. The surgeon may then pull the retraction cables to enable the upper and lower retainer lugs 716, 726 to extend into the respective openings 616 and 626 in the clip 600 to thereby enable the clip to be pushed into the distal direction "DD" by a discharge member, bar, surgical tool inserted through the discharge lumen in the endoscope. Again the surgeon releases the grasper from the tissue and retrieves the grasper from the working channel. The clip 600 remains installed on the tissue and the endoscope may then be withdrawn from the patient to enable another clip 600 to be installed on the adapter if addition clips are required and the process then be repeated again.

Figure 25:
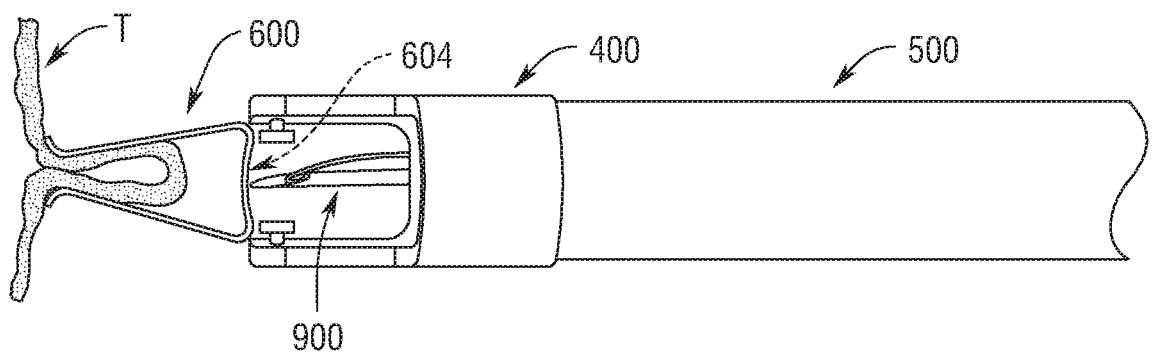
FIG. 25 is a side view of a clip and clip dispenser embodiment of the present invention being employed with a tissue anchor applier.

Another feature of clip 600 is the ability to facilitate the installation of tissue anchors or sutures to the clipped tissue by passing a tissue anchor applier 900 through the endoscope 500 and through the hole 604 in the clip 600 as shown in FIG. 25. A variety of such tissue anchor appliers are known. For example, tissue anchor applier 900 may comprise any of the tissue anchor applying devices disclosed in any of the following cited documents, the disclosures of which are each herein incorporated by reference in their respective entireties: (i) U.S. Patent Application Publication No. 2008/0103527 A1 to David T. Martin et al., entitled "Flexible Endoscopic Suture Anchor Applier", Ser. No. 11/553,489, filed Oct. 27, 2006. (ii) U.S. Patent Application Publication No. 2007/0270907 A1, to Michael J. Stokes et al., entitled "Suture Locking Device", Ser. No. 11/437,440, filed May 19, 2006, (iii) U.S. Patent No. 2007/0270889 A1 to Sean P. Conlon et al., entitled "Combination Knotting Element and Suture Anchor Applicator", Ser. No. 11/437,864, filed May 19, 2006, which issued on Jul. 20, 2010 as U.S. Pat. No. 7,758,598, and (iv) pending co-owned U.S. patent application Ser. No. 11/796,035 to David Stefanchik et al., entitled "Surgical Suturing Apparatus", filed Apr. 26, 2007, which issued on Dec. 13, 2011 as U.S. Pat. No. 8,075,572. As can be seen in FIG. 25, the needle portion 902 of the tissue anchor applier 900 is introduced through the endoscope 500 to enable it to pierce through the tissue "T" on both sides of the opening. For example, when the opening comprises a gastrotomy, the needle 902 of the tissue anchor applier 900 may be able to pierce the tissue "T" on both sides of the gastrotomy while remaining in the stomach. This may be a significant safety advantage when compared to use of prior closure systems. For example, when employing prior closure systems and methods, a mucosa-mucosa apposition is created. When employing the clip 600 of the present invention, a serosa-to-serosa apposition is created which may result in a more secure/permanent healing of the gastrotomy.

As can be readily appreciated from the foregoing, the various embodiments of the present invention described above represent a vast improvement over prior devices and methods used to apply tissue apposition clips for closing gastrotomies. The unique and novel features of the various embodiments of the present invention enable the operation to be performed through a natural orifice in the patient and thereby avoid several disadvantages associated with other conventional surgical methods and procedures that require incisions to be made into the abdomen. The present invention may comprise a device that contains several clips that may be serial advanced onto tissue that is grasped and manipulated using conventional tissue grasping devices. Other embodiments may comprise a clip dispensing adapter that may be applied to a distal end of a conventional endoscope and, if desired, supplied and/or sold separately from the endoscope. Such adapters may be pressed onto, threaded onto or otherwise temporarily attached to the distal end of the endoscope to complete the above-described procedure and thereafter removed from the endoscope and discarded or reprocessed for future use. Other embodiments of the present invention contemplate permanent attachment of the adapter to the distal end of the endoscope and still other embodiments envision that the adapter may be integrally formed on the distal end of the endoscope.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the inventions described herein will be processed before surgery. First a new or used endoscope is obtained and, if necessary, cleaned. The endoscope can then be sterilized. In one sterilization technique, the endoscope is placed in a closed and sealed container, such as a plastic or TYVEK® bag. The container and endoscope are then placed in a field of radiation that can penetrate the container, such as gamma radiation, x-rays, or higher energy electrons. The radiation kills bacteria on the endoscope and in the container. The sterilized endoscope can then be stored in the sterile container. The sealed container keeps the endoscope sterile until it is opened in the medical facility.

Any patent, publication, application or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. The claim has been replaced with

A clip application device for treating tissue, the clip application device comprising:
 a flexible tube comprising a remotely articulatable end portion;
 a clip magazine having a clip passage therein, wherein the clip magazine is insertable in the flexible tube;
 tissue apposition clips stored in the clip passage in a biased-open configuration;
 an advancement member for applying an advancement motion to the tissue apposition clips in the clip passage to cause the tissue apposition clips to move out of said clip passage;
 a first grasper extending from the flexible tube and configured to grasp the tissue; and
 a second grasper extending from the flexible tube and configured to grasp the tissue,
 wherein the tissue apposition clips are deployable over the first and second graspers to clip the tissue.

2. The clip application device of claim 1, wherein the tissue apposition clips are movable by the advancement member in the clip passage in the biased-open configuration.

3. The clip application device of claim 1, wherein the first and second graspers are movable relative to the tissue apposition clips.

4. The clip application device of claim 1, wherein each of the tissue apposition clips comprises two clip arms biased away from each other in the clip passage.

5. The claim has been replaced with

A surgical system for treating tissue, the surgical system comprising:
 a control unit;
 a flexible tube comprising an end portion remotely articulatable by the control unit;
 a clip magazine having a clip passage therein, wherein the clip magazine is insertable in the flexible tube;
 tissue apposition clips stored in the clip passage in a biased-open configuration;
 an advancement member for applying an advancement motion to the tissue apposition clips in the clip passage to cause the tissue apposition clips to move out of said clip passage;
 a camera positioned at the end portion, wherein the tissue apposition clips are advanceable distally beyond the camera;
 a first grasper extending from the flexible tube and configured to grasp the tissue; and
 a second grasper extending from the flexible tube and configured to grasp the tissue,
 wherein the tissue apposition clips are deployable over the first and second graspers to clip the tissue.

6. The surgical system of claim 5, wherein the tissue apposition clips are movable by the advancement member in the clip passage in the biased-open configuration.

7. The surgical system of claim 5, wherein the first and second graspers are movable relative to the tissue apposition clips.

8. The surgical system of claim 5, wherein each of the tissue apposition clips comprises two clip arms biased away from each other in the clip passage.

9. The claim has been replaced with

A surgical system for treating tissue, the surgical system comprising:
 a control unit;
 a flexible tube comprising an end portion remotely articulatable by the control unit, wherein the flexible tube defines a clip passage;
 tissue apposition clips stored in the clip passage in a biased-open configuration;
 an advancement member for applying an advancement motion to the tissue apposition clips in the clip passage to cause the tissue apposition clips to move out of said clip passage;
 a camera positioned at the end portion, wherein the tissue apposition clips are advanceable distally beyond the camera;
 a first grasper extending from the flexible tube and configured to grasp the tissue; and
 a second grasper extending from the flexible tube and configured to grasp the tissue,
 wherein the tissue apposition clips are deployable over the first and second graspers to clip the tissue.

10. The surgical system of claim 9, wherein the tissue apposition clips are movable by the advancement member in the clip passage in the biased-open configuration.

11. The surgical system of claim 9, wherein the first and second graspers are movable relative to the tissue apposition clips.

12. The surgical system of claim 9, wherein each of the tissue apposition clips comprises two clip arms biased away from each other in the clip passage.

* * * * *